United States Patent
Hergenrother et al.

(10) Patent No.: US 12,234,240 B2
(45) Date of Patent: *Feb. 25, 2025

(54) SUBSTITUTED IMIDAZO[5,1-D][1,2,3,5]TETRAZINES FOR THE TREATMENT OF CANCER

(71) Applicant: The Board of Trustees of the University of Illinois, Urbana, IL (US)

(72) Inventors: Paul J. Hergenrother, Champaign, IL (US); Timothy M. Fan, Mahomet, IL (US); Riley L. Svec, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,531

(22) Filed: Dec. 16, 2022

(65) Prior Publication Data

US 2023/0183252 A1 Jun. 15, 2023
US 2024/0124462 A9 Apr. 18, 2024

Related U.S. Application Data

(63) Continuation of application No. 17/017,475, filed on Sep. 10, 2020, now abandoned, which is a continuation-in-part of application No. PCT/US2019/045986, filed on Aug. 9, 2019.

(60) Provisional application No. 62/873,669, filed on Jul. 12, 2019, provisional application No. 62/778,750, filed on Dec. 12, 2018, provisional application No. 62/716,390, filed on Aug. 9, 2018.

(51) Int. Cl.
| | |
|---|---|
| *A61K 31/519* | (2006.01) |
| *A61K 9/20* | (2006.01) |
| *A61K 9/48* | (2006.01) |
| *A61K 31/495* | (2006.01) |
| *A61K 47/02* | (2006.01) |
| *A61K 47/24* | (2006.01) |
| *A61K 47/26* | (2006.01) |
| *A61K 47/34* | (2017.01) |
| *A61K 47/36* | (2006.01) |
| *C07D 487/04* | (2006.01) |

(52) U.S. Cl.
CPC .......... *C07D 487/04* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/485* (2013.01); *A61K 9/4858* (2013.01); *A61K 9/4866* (2013.01); *A61K 31/495* (2013.01); *A61K 47/02* (2013.01); *A61K 47/24* (2013.01); *A61K 47/26* (2013.01); *A61K 47/34* (2013.01); *A61K 47/36* (2013.01)

(58) Field of Classification Search
CPC .......................... A61K 31/519; C07D 487/04
USPC ....................... 514/262.1; 544/262
See application file for complete search history.

(56) References Cited

U.S. PATENT DOCUMENTS

| | | |
|---|---|---|
| 5,260,291 A | 11/1993 | Lunt et al. |
| 7,173,021 B2 | 2/2007 | Wang et al. |
| 7,446,209 B2 | 11/2008 | Kuo et al. |
| 7,612,202 B2 | 11/2009 | Etlin et al. |
| 8,450,479 B2 | 5/2013 | Stevens et al. |
| 9,024,018 B2 | 5/2015 | Hummersone et al. |
| 9,320,807 B2 | 4/2016 | Patil et al. |
| 9,629,919 B2 | 4/2017 | Patil et al. |
| 2005/0203082 A1 | 9/2005 | Hsu et al. |
| 2006/0183898 A1 | 8/2006 | Etlin et al. |
| 2008/0044457 A1 | 2/2008 | Wang |

(Continued)

FOREIGN PATENT DOCUMENTS

| | | |
|---|---|---|
| CN | 101190917 A | 6/2008 |
| CN | 101945874 A | 1/2011 |

(Continued)

OTHER PUBLICATIONS

Furiassi, L., "Medicinal Chemistry Approaches to Widen Therapeutic Potential for Melatonin and Temozolomide Derivatives", University of Urbino, created Apr. 25, 2018. Retrieved from internet: 1-123 (Year: 2021).

(Continued)

*Primary Examiner* — Douglas M Willis
(74) *Attorney, Agent, or Firm* — Haukaas Fortius PLLC; Michael Haukaas

(57) ABSTRACT

New synthetic methods to provide access to previously unexplored functionality at the C8 position of substituted imidazo[5,1-d][1,2,3,5]tetrazines of Formula I. Through synthesis and evaluation of a suite of compounds with a range of aqueous stabilities (from 0.5 to 40 hours), a predictive model for imidazotetrazine hydrolytic stability based on the Hammett constant of the C8 substituent was derived. Promising compounds were identified that possess activity against a panel of GBM cell lines, appropriate hydrolytic and metabolic stability, and brain-to-serum ratios dramatically elevated relative to TMZ, leading to lower hematological toxicity profiles and superior activity to TMZ in a mouse model of GBM.

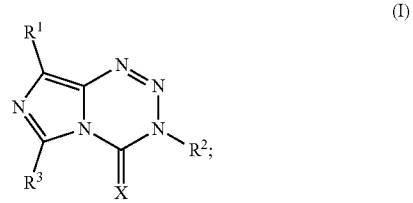

(I)

13 Claims, 12 Drawing Sheets

(56) References Cited

U.S. PATENT DOCUMENTS

| | | | |
|---|---|---|---|
| 2012/0083513 | A1 | 4/2012 | Hummersone et al. |
| 2013/0012706 | A1 | 1/2013 | Hummersone et al. |
| 2013/0338104 | A1 | 12/2013 | Stevens et al. |
| 2016/0199302 | A1 | 7/2016 | Lim et al. |
| 2017/0042886 | A1 | 2/2017 | Hergenrother et al. |
| 2021/0002286 | A1 | 1/2021 | Hergenrother et al. |
| 2021/0315886 | A1 | 10/2021 | Hergenrother et al. |

FOREIGN PATENT DOCUMENTS

| | | |
|---|---|---|
| EP | 0252682 A3 | 1/1990 |
| JP | 2008513523 A | 5/2008 |
| JP | 2011506588 A | 3/2011 |
| JP | 2012530775 A | 12/2012 |
| JP | 6366182 B2 | 8/2018 |
| KR | 1020070062569 B1 | 9/2011 |
| WO | 2010149968 A1 | 12/2010 |

OTHER PUBLICATIONS

Gyanani et al., "Challenges of Current Anticancer Treatment Approaches with Focus on Liposomal Drug Delivery Systems", Pharmaceuticals, 14, 835, Aug. 2021.

International Search Report and Written Opinion of the ISA/US dated Jun. 28, 2023 in International Application No. PCT/US2023/061774; 9pgs.

Kaestner et al., "Chemotherapy Dosing Part I: Scientific Basis for Current Practice and Use of Body Surface Area", Clinical Oncology 19: 23-37, Feb. 2007.

Larsson et al., "Optimization of cell viability assays to improve replicability and reproducibility of cancer drug sensitivity screens", Sci Rep, vol. 10, Article 5798; 1-12, Apr. 2020.

Sadchikova, E.V., "Synthesis of new azolo[5,1-d] [1,2,3,5]tetrazin-4-ones—analogs of antitumor agent temozolomide", Russ.Chem. Bull., Int. Ed., vol. 65, No. 7, 1867-1872, Jul. 2016.

Stevens, et al., "Antitumor Imidazotetrazines. 1. Synthesis and Chemistry of 8-Carbamoyl-3-(2-chloroethyl)imidazo [5,1-d]-1,2,3,5-tetrazin-4(3H)-one, a Novel Broad-Spectrum Antitumor Agent", J. Med. Chem., 27, 196-201, Feb. 1984.

Bouzinab et al., "Delivery of Temozolomide and N3-Propargyl Analog to Brain Tumors Using an Apoferritin Nanocage", ACS Appl. Mater. Interfaces 2020, Feb. 2020, 12, 12609-12617.

Cho et al., "NEO212, Temozolomide Conjugated to Perillyl Alcohol, is a Novel Drug for Effective Treatment of a Broad Range of Temozolomide-Resistant Gliomas," Mol Cancer Ther., 13(8), pp. 44, Jul. 2014.

Clark et al., "Antitumor Imidazotetrazines. 32. Synthesis of Novel Imidazotetrazinones and Related Bicyclic Heterocycles to Probe the Mode of Action of the Antitumor Drug Temozolomide", J. Med. Chem. 1995, Nov. 23, 1994, 38, pp. 1493-1504.

Cousin et al., "Antitumor imidazoij5, 1-d]-1,2,3,5-tetrazines: compounds modified at the 3-position overcome resistance in human glioblastoma cell lines", Med. Chem. Commun., Sep. 15, 2016, 7, 2332.

Cousin et al., "Antitumour imidazotetrazines. Synthesis and chemistry of 4-oxo-3,4-dihydroimidazo[5, 1-d][1,2,3,5] tetrazine-8-carboxamide (nor-temozolomide): an intermediate for the preparation of the antitumour drug temozolomide and analogues, avoiding the use of isocyanates", Med. Chem. Commun., 2012, Sep. 11, 2012, 3, 1419.

Denny et al., "NMR and Molecular Modeling Investigation of the Mechanism of Activation of the Antitumor Drug Temozolomide and Its Interaction with DNA," Biochemistry, 33(31):9045-9051, Aug. 1994.

Extended Search Report and Written Opinion of the European Patent Office dated Jun. 15, 2022 in EP Application No. 19848070.9; 12pgs.

Horspool et al., "Antitumor Imidazotetrazines. 20.1 Preparation of the 8-Acid Derivative of Mitozolomide and Its Utility in the Preparation of Active Antitumor Agents," J. Med. Chem., 33(5):1393-1399, May 1990.

International Search Report and Written Opinion of International Application No. PCT/US2019/045986, dated Dec. 3, 2019, 11pgs.

Langnel et al., "Anti Tumor Imidazotetrazines. 38. New 8-Substituted Derivatives of the imidazo[S, L-D]-1,2, 3,5-Tetrazines Temozolomide and Mitozolomide," Archive for Organic Chemistry (Arkivoc), 2000(3):421-437, Aug. 2000.

Lowe et al., "Antitumor Imidazotetrazines. 25.1 Crystal Structure of 8-Carbamoyl-3-methylimidazo[5,I-tf]-1,2,3,5-tetrazin-4(3fl>one (Temozolomide) and Structural Comparisons with the Related Drugs Mitozolomide and DTIC," J Med Chem., 35(18):3377-3382, Sep. 1992.

Lunt et al., "Antitumor Imidazotetrazines. 14. Synthesis and Antitumor Activity of 6- and 8-Substituted imidazo[5,1-D]-1,2, 3,5-Tetrazinones and 8-Substituted pyrazolo[5,1-D]-1,2, 3,5-Tetrazinones," J Med Chem., 30(2):357-366, Feb. 1987.

McFaline-Figueroa et al., "Minor Changes in Expression of the Mismatch Repair Protein MSH2 Exert a Major Impact on Glioblastoma Response to Temozolomide", Cancer Res. Aug. 2015. 1;75(15):3127-38.

Partial Extended Search Report of the European Patent Office dated Mar. 14, 2022 in EP Application No. 19848070.9; 14pgs.

Pubchem, Substance Record for SID 332875295, Available Date: Apr. 11, 2017, 4 pages, from https://pubchem.ncbi.nlm.nih.gov/substance/332875295.

Suppasansatorn et al., "Skin Delivery Potency and Antitumor Activities of Temozolomide Ester Prodrugs," Cancer Lett., 244(1):42-52, Nov. 2006.

Svec et al., "Tunable Stability of Imidazotetrazines Leads to a Potent Compound for Glioblastoma", ACS Chem. Biol. 2018, 13, pp. 3206-3216.

Wang et al., "Antitumor Imidazotetrazines. 35. New Synthetic Routes to the Antitumor Drug Temozolomide," J. Org. Chem., 62(21):7288-7294, Oct. 1997.

Wang et al., "Antitumour imidazotetrazines. Part 36. Conversion of 5-amino-imidazole-4-carboxamide to imidazo [5,1-d][1,2,3,5]tetrazin-4(3H)-ones and imidazo[1,5-a][1,3,5]triazin-4(3H)-ones related in structure to the antitumour agents temozolomide and mitozolomide", J. Chem. Soc., Perkin Trans. 1, Jan. 1, 1998, pp. 1669-1676.

Zhang et al., "N3-Substituted Temozolomide Analogs Overcome Methylguanine-DNA Methyltransferase and Mismatch Repair Precipitating Apoptotic and Autophagic Cancer Cell Death", Oncology 2015; Sep. 2014; 88:28-48.

Zhang et al., "Temozolomide: Mechanisms of Action, Repair and Resistance", Curr Mol Pharmacol. Jan. 2012;5(1):102-14.

Welch et al., "Morphologic, Immunologic, Biochemical, and Cytogenetic Characteristics of the Human Glioblastoma-Derived Cell Line, SNB-19," In Vitro Cell. Dev. Biol. Animal 31:610-616, Sep. 1995.

Patani, et al., "Bioisosterism: a rational approach in drug design." Chemical reviews 96.8: 3147-3176, Dec. 1996.

a)

b)

SUBSTITUTED IMIDAZO[5,1-D][1,2,3,5]TETRAZINES FOR THE TREATMENT OF CANCER

RELATED APPLICATIONS

This application is a continuation of U.S. patent application Ser. No. 17/017,475, filed Sep. 10, 2020, which is a continuation-in-part of International Application No. PCT/US2019/045986 filed Aug. 9, 2019, which claims priority under 35 U.S.C. § 119(e) to U.S. Provisional Patent Application Nos. 62/716,390 filed on Aug. 9, 2018, 62/778,750 filed on Dec. 12, 2018, and 62/873,669 filed on Jul. 12, 2019, each of which are incorporated herein by reference in their entirety.

GOVERNMENT SUPPORT

This invention was made with government support under Grant No. R21-CA195149 awarded by the National Institutes of Health. The government has certain rights in the invention.

BACKGROUND OF THE INVENTION

Glioblastoma multiforme (GBM) is the most prevalent, infiltrative, and lethal primary malignant brain tumor, with only 10% of patients surviving five years.[1] The current standard-of-care for GBM is gross surgical resection followed by radiotherapy combined with temozolomide (TMZ), a small molecule DNA alkylating agent. The antitumor effect of TMZ is ultimately mediated through methylation of the $O^6$-position of guanine residues and subsequent mismatch repair-dependent cell death.[2-6] Among the beneficial properties of TMZ are favorable pharmacokinetics (including 100% oral bioavailability[7]), non-enzymatic prodrug activation, and some accumulation in the brain (cerebral spinal fluid:blood ratio of 17:83 in human cancer patients[8,9]). TMZ provides a significant therapeutic benefit to a subset of GBM patients. For example, in patients whose tumors do not express $O^6$-methylguanine DNA methyltransferase (MGMT), an enzyme that removes $O^6$-methylguanine lesions, TMZ extends median survival to approximately two years.[10] Even in the era of personalized anticancer therapy, TMZ remains frontline therapy for oligodendrogliomas, diffuse astrocytic gliomas, and pleomorphic xanthoastrocytomas in addition to GBM.[11] However, given the ineffectiveness of TMZ against tumors expressing MGMT and the inevitable recurrence of GBM after multimodal combination therapy, there remains a significant clinical need for better treatment strategies.

TMZ is a prodrug activated in aqueous solutions that ultimately releases methyl diazonium, the active alkylating component (Scheme 1(a)). The half-life of TMZ is ~2 hours in vivo and in aqueous solutions in vitro, and it has been suggested that the drug has an increased rate of hydrolysis in the more alkaline environment of gliomas, providing some selectivity for cancerous vs. non-cancerous cells.[12-15] While this 2 hour half-life enables TMZ to reach the central nervous system (CNS) and release methyldiazonium, there is scarce information on the relationship between half-life and anticancer activity; specifically, it is unclear if 2 hours is optimal to maximize therapeutic efficacy or if shorter (or longer) half-lives may bolster its effect. Given the advantageous features of TMZ, an understanding of the relationship between its structure, hydrolytic stability, and anticancer activity.

While TMZ has been FDA approved for two decades, more efficacious drugs for glioblastoma that have lower systemic toxicity would be desirable. Therapeutic compounds that can reach the entirety of the diffuse tumor in sufficient concentrations to be effective are sought. Accordingly, there is a need for new compounds that possess the desirable properties of TMZ, but have better brain penetration, lower toxicity, and provide improved patient survival rates.

SUMMARY

Herein is described the development of a model that accurately predicts the hydrolytic stability and half-life of imidazotetrazines. This model was used to discover novel imidazotetrazines with exceptional BBB penetration and superior anticancer activity compared to TMZ, including in a murine model of GBM.

Accordingly, this disclosure provides a compound of Formula I:

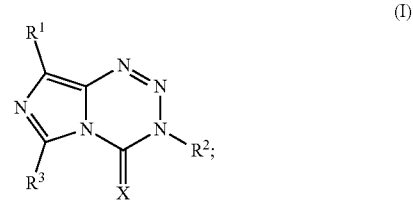

or a salt thereof;
wherein
X is O or S;
$R^1$ is halo, —CN, —NO$_2$, —(C$_1$-C$_6$)alkyl, —C(=O)R$^a$, phenyl, or a 5- or 6-membered heterocycle, wherein R$^a$ is H, halo, —(C$_1$-C$_6$)alkyl, —(C$_3$-C$_6$)cycloalkyl, OR$^b$, SR$^b$, or —NR$^b$R$^c$; wherein
$R^b$ is H, —(C$_1$-C$_6$)alkyl, or —(C$_3$-C$_6$)cycloalkyl;
$R^c$ is H, —(C$_1$-C$_6$)alkyl, or —(C$_3$-C$_6$)cycloalkyl; or
when R$^a$ is —NR$^b$R$^c$, R$^b$ and R$^c$ taken together optionally forms a heterocycle;
$R^2$ is —(C$_1$-C$_6$)alkyl, —(C$_3$-C$_6$)cycloalkyl, alkynyl, phenyl, or a 5- or 6-membered heterocycle; and
$R^3$ is H, —(C$_1$-C$_6$)alkyl, or —(C$_3$-C$_6$)cycloalkyl;
wherein each —(C$_1$-C$_6$)alkyl, —(C$_3$-C$_6$)cycloalkyl, alkynyl, phenyl, and 5- or 6-membered heterocycle are optionally substituted with one or more substituents, and each —(C$_1$-C$_6$)alkyl is unbranched or optionally branched.

This disclosure also provides a method of treating a cancer comprising administering to a subject in need thereof a therapeutically effective amount of the compound disclosed above, wherein the cancer is thereby treated.

The invention provides novel compounds of Formulas I-III(A/B/C), intermediates for the synthesis of compounds of Formulas I-III, as well as methods of preparing compounds of Formulas I-III. The invention also provides compounds of Formulas I-III that are useful as intermediates for the synthesis of other useful compounds. The invention provides for the use of compounds of Formulas I-III for the manufacture of medicaments useful for the treatment of bacterial infections in a mammal, such as a human.

The invention provides for the use of the compositions described herein for use in medical therapy. The medical therapy can be treating cancer, for example, bladder cancer, breast cancer, colon cancer, endometrial cancer, kidney (renal) cancer, leukemia, lung cancer, lymphoma, Non-Hodgkin's lymphoma, melanoma, pancreatic cancer, prostate cancer, non-melanoma skin cancer, stomach cancer, thyroid cancer, or brain cancers such as glioblastoma. The invention also provides for the use of a composition as described herein for the manufacture of a medicament to treat a disease in a mammal, for example, cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
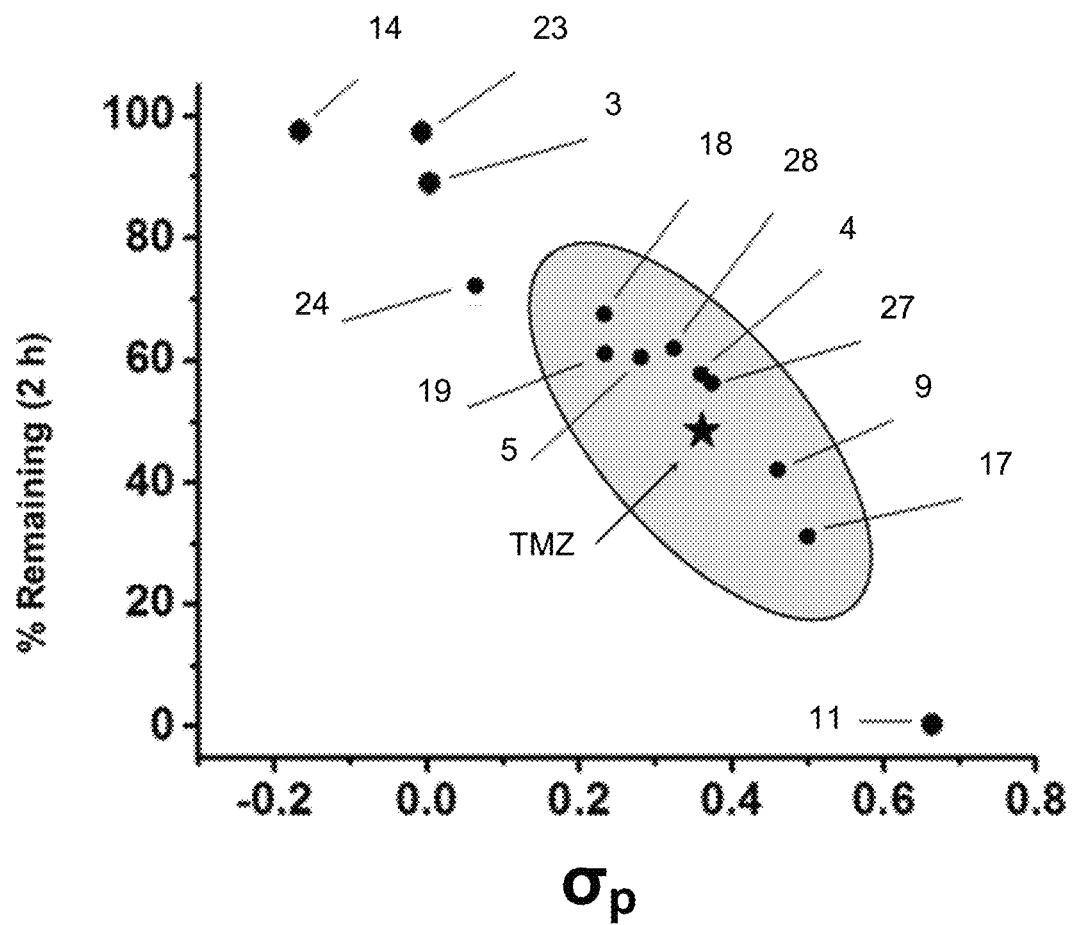
FIG. 1. Hydrolytic stability of C8-substituted imidazotetrazines. (a) The percentage of compound remaining after 2 hours plotted against the Hammett constant of its C8 substituent. Compounds with hydrolytic stability similar to TMZ are enclosed in the oval (see Table 1c).

Even in the era of personalized medicine and immunotherapy, temozolomide (TMZ), a small molecule DNA alkylating agent, remains the standard-of-care for glioblastoma (GBM). TMZ has an unusual mode-of-action, spontaneously converting to its active component via hydrolysis in vivo. While TMZ has been FDA approved for two decades, it provides little benefit to patients whose tumors express the resistance enzyme MGMT and gives rise to systemic toxicity through myelosuppression. TMZ was first synthesized in 1984, but certain key derivatives have been inaccessible due to the chemical sensitivity of TMZ, precluding broad exploration of the link between imidazotetrazine structure and biological activity. Therefore, discerning the relationship between the hydrolytic stability and anticancer activity of imidazotetrazines, with the objectives of identifying optimal timing for prodrug activation and developing suitable compounds with enhanced efficacy via increased blood-brain barrier penetrance was sought.

This work necessitated the development of new synthetic methods to provide access to previously unexplored functionality (such as aliphatic, ketone, halogen, and aryl groups) at the C8 position of imidazotetrazines. Through synthesis and evaluation of a suite of compounds with a range of aqueous stabilities (from 0.5 to 40 hours), a predictive model for imidazotetrazine hydrolytic stability based on the Hammett constant of the C8 substituent was derived. Promising compounds were identified that possess activity against a panel of GBM cell lines, appropriate hydrolytic and metabolic stability, and brain-to-serum ratios dramatically elevated relative to TMZ leading to lower hematological toxicity profiles and superior activity to TMZ in a mouse model of GBM. This work points a clear path forward for the development of novel and effective anticancer imidazotetrazines.

While the amide at C8 of TMZ had been suggested in the past to be essential for activity,[2,16] conflicting reports have since indicated that alternate functionality may be tolerated at this position.[17-19] Indeed, an analysis led to a belief that strategic substitutions at C8 could be used to tune the hydrolytic stability of imidazotetrazines, and that in doing so a suite of compounds with a range of half-lives could be constructed. In addition to varying the stability of the prodrug, alterations at the C8 position could lead to compounds that retain the favorable pharmacokinetic properties of TMZ but have increased CNS penetrance. An imidazotetrazine with enhanced blood-brain barrier (BBB) penetrance will exhibit lower systemic toxicity and allow for higher and more efficacious dosing regimens since the dose-limiting toxicity of TMZ (myelosuppression) is not CNS-related.[7,20,21]

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject. The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms or a range in between (such as 2-8 or 3-8 carbons), and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups in various embodiments. An alkynyl group can be, for example, acetylene (—C≡CH), propargyl (—CH$_2$C≡CH), butynyl (e.g., —CH$_2$CH$_2$C≡CH or —CH$_2$C≡CCH$_3$), or other alkynyl groups having 5-10 carbon atoms. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, p-carbolinyl, carbazolyl, chromenyl, cinnolinyl, dibenzo[b, d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or (C$_1$-C$_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

EMBODIMENTS OF THE INVENTION

This disclosure provides a compound of Formula I:

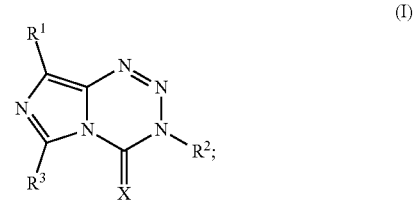

or a salt thereof;

wherein
X is O or S;
R[1] is halo, —CN, —NO$_2$, —(C$_1$-C$_6$)alkyl, —C(=O)R$^a$, phenyl, or a 5- or 6-membered heterocycle, wherein R$^a$ is H, halo, —(C$_1$-C$_6$)alkyl, —(C$_3$-C$_6$)cycloalkyl, OR$^b$, SR$^b$, or —NR$^b$R$^c$; wherein
R$^b$ is H, —(C$_1$-C$_6$)alkyl, or —(C$_3$-C$_6$)cycloalkyl;
R$^c$ is H, —(C$_1$-C$_6$)alkyl, or —(C$_3$-C$_6$)cycloalkyl; or when R$^a$ is —NR$^b$R$^c$, R$^b$ and R$^c$ taken together optionally forms a heterocycle;
R$^2$ is —(C$_1$-C$_6$)alkyl, —(C$_3$-C$_6$)cycloalkyl, alkynyl, phenyl, or a 5- or 6-membered heterocycle; and
R$^3$ is H, —(C$_1$-C$_6$)alkyl, or —(C$_3$-C$_6$)cycloalkyl;
wherein each —(C$_1$-C$_6$)alkyl, —(C$_3$-C$_6$)cycloalkyl, alkynyl, phenyl, and 5- or 6-membered heterocycle are optionally substituted with one or more substituents, and each —(C$_1$-C$_6$)alkyl is unbranched or optionally branched.

In some embodiments, the phenyl and —(C$_1$-C$_6$)alkyl are each independently substituted with, for example but not limited to, halo (e.g., one or more chloro or fluoro), alkoxy, or aminoalkyl. In some other embodiments the substituents do not include a phenyl group, or the molecular weight of the substituent is less than about 100, about 90, about 80, about 70, about 60, or about 50. In yet other embodiments, both R$^b$ and R$^c$ cannot be H.

In other embodiments, R[1] is —C(=O)—(C$_1$-C$_6$)alkyl, —C(=O)—NH(C$_1$-C$_6$)alkyl, or —C(=O)—N[(C$_1$-C$_6$)alkyl]$_2$. In further In other embodiments, X is O, R$^3$ is H and R[1] is —C(=O)—(C$_1$-C$_6$)alkyl, —C(=O)—NH(C$_1$-C$_6$)alkyl, or —C(=O)—N[(C$_1$-C$_6$)alkyl]$_2$. In yet other embodiments, X is O and R[1] is —C(=O)—(C$_1$-C$_6$)alkyl. In additional embodiments, X is O, R$^2$ is —(C$_1$-C$_6$)alkyl, and R$^3$ is H. In some other embodiments, R$^2$ is —(C$_1$-C$_6$)alkyl and R$^3$ is H. In various other embodiments, R$^2$ is propargyl or a substituted phenyl. In some embodiments, X is O and R$^3$ is H.

In various embodiments, R' is a moiety of Formula IB:

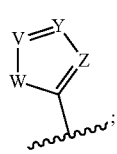

(IB)

wherein
W is O, S, or NR$^d$; wherein R$^d$ is H, —(C$_1$-C$_6$)alkyl, or —(C$_3$-C$_6$)cycloalkyl;
V is N or CR$^x$, wherein R$^x$ is H, —(C$_1$-C$_6$)alkyl, or —(C$_3$-C$_6$)cycloalkyl;
Y is N or CR$^y$, wherein R$^y$ is H, —(C$_1$-C$_6$)alkyl, or —(C$_3$-C$_6$)cycloalkyl; and
Z is N or CH.

In various other embodiments, R[1] is one of:

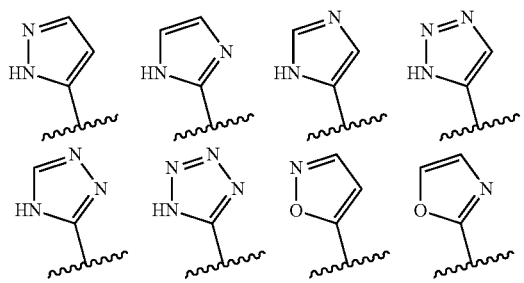

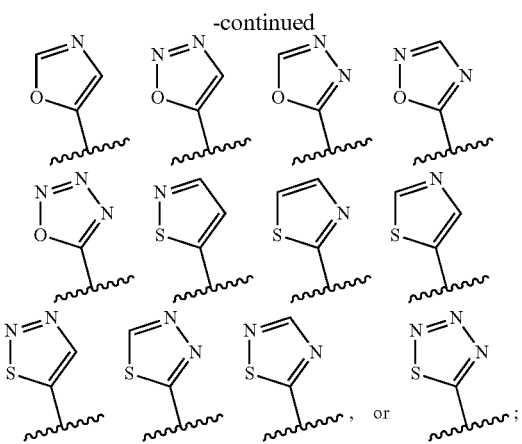

wherein the 5-membered heterocyclic moiety R[1] is optionally substituted (at one or the other of the carbon atoms CH, thereby modifying that carbon to C-substituent, wherein the substituent is a substituent as defined herein).

In further embodiments, R[1] is i, ii, or iii:

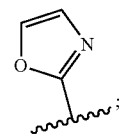

(i)

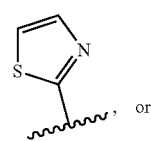

(ii)

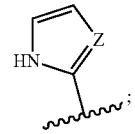

(iii)

wherein (i), (ii) and (iii) are optionally substituted at position 4 or 5.

In additional embodiments, R[1] is a para-substituted phenyl, wherein the molecular weight of each substituent is less than about 300, about 200 or about 100 daltons. In yet other embodiments, the para-substituent is halo, —CN, —CF$_3$, —CF$_2$CF$_3$, or —(C$_1$-C$_6$)alkyl. In some other embodiments, R[1] is halo, —(C$_1$-C$_6$)alkyl, or —(C$_3$-C$_6$)cycloalkyl.

In various additional embodiments, the substituted phenyl is substituted with halo, alkyl, alkoxy, phenoxy, amine, alkylamine, dialkylamine, or combination thereof.

In other embodiments, the compound is:

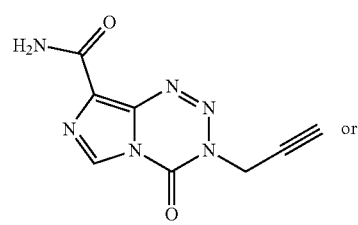

or

-continued

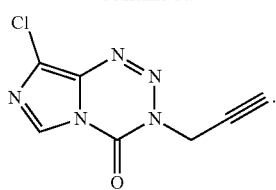

In additional embodiments, the compound of Formula I is a compound of Formula IC:

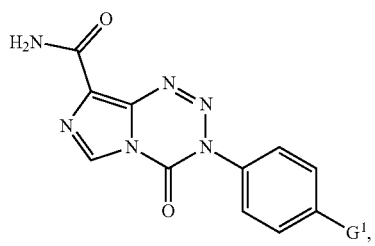

(IC)

wherein G¹ is halo, alkyl, alkoxy, phenoxy, or dialkylamine. In some embodiments G¹ is OCH₃, OCH₂CH₃, OPh, or N(CH₃)₂.

In various other embodiments, the compound of Formula I is a compound of Formula II:

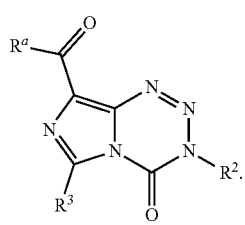

(II)

In additional embodiments, $R^2$ is —$(C_1-C_6)$alkyl and $R^3$ is H. In yet other embodiments, the compound is K-TMZ:

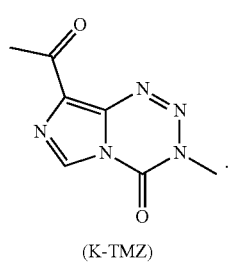

(K-TMZ)

In further embodiments, $R^a$ is $CH_3$, $CH_2CH_3$, $NHCH_3$, $NHCH_2CH_3$, $N(CH_3)_2$, $N(CH_2CH_3)_2$, $N(CH_2CH_2CH_3)_2$, $N(CH_2CH_2CH_2CH_3)_2$, $N(CH_2CH_2)_2$, $N[(CH_2CH_2)_2O]$, $OCH_3$, $OCH_2CH_3$, $SCH_3$, or $SCH_2CH_3$. In other embodiments, the compound is:

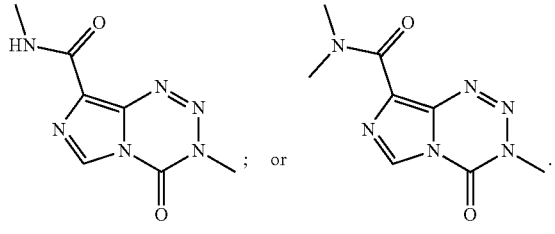

(Me-TMZ)   (DiMe-TMZ)

In additional embodiments, the compound of Formula I is a compound of Formula IIIA or IIIB:

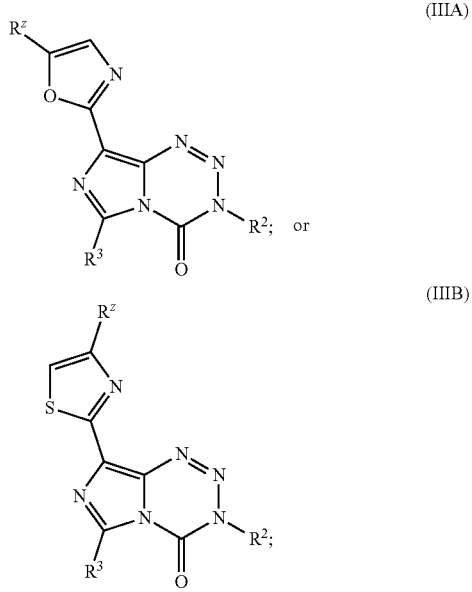

(IIIA)

(IIIB)

wherein $R^z$ is H, halo, —$(C_1-C_6)$alkyl, or —$(C_3-C_6)$cycloalkyl. In other embodiments, $R^z$ is $CH_3$ or $CH_2CH_3$. In yet other embodiments, the compound is:

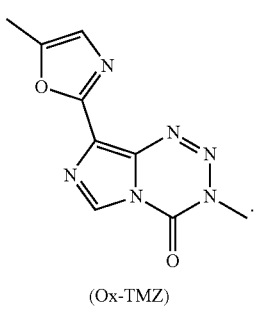

(Ox-TMZ)

This disclosure additionally provides a method of treating a cancer comprising administering to a subject in need thereof a therapeutically effective amount of the compound of any formula described herein, wherein the cancer is thereby treated. In other additional embodiments, the cancer is glioblastoma (GBM).

In some embodiments, a composition comprises the compounds disclosed above and a second active agent. In other embodiments, the second active agent is a procaspase-3 activator, for example PAC-1:

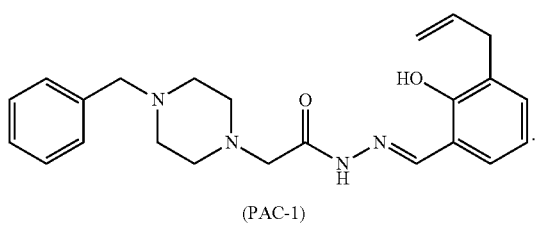 [SMILES: C=CCc1cccc(/C=N/NC(=O)CN2CCN(Cc3ccccc3)CC2)c1O]

(PAC-1)

In yet further embodiments, the disclosed compounds herein and the second active agent are administered to a subject concurrently or sequentially for the treatment of a cancer. In some additional embodiments, the disclosed compound and the second active agent are concurrently administered to the subject. In other embodiments, the disclosed compound and the second active agent are sequentially administered to the subject. In some other embodiments, the disclosed compound is administered to the subject before the second active agent. In yet more embodiments, the disclosed compound is administered to the subject after the second active agent.

In some embodiments, the concentration of the disclosed compounds herein is about 1 nM to about 10 μM, or corresponding mg active agent/kg body weight of the subject, as would be recognized by one of skill in the art. In yet other embodiments, the concentration of the second active agent is about 1 nM to about 1 μM.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion.

Construction of C8-substituted imidazotetrazines. The inclusion of an amide at the C8 position of TMZ is largely an artifact of the original synthesis of imidazotriazenes and imidazotetrazines. Both dacarbazine and TMZ are derived from precursor 4-diazoimidazole-5-carboxamide (1, Scheme 1b). The remarkable stability of this diazo species, reportedly >2.5 years at room temperature,[22] permitted its use for exploratory chemistry where other diazoimidazole species (such as 4-diazoimidazole (2)) simply decomposed.[23] Thus, the initial synthesis of dacarbazine in 1962 and TMZ in 1984 involved the quenching of 1 with dimethylamine[24] or the cyclization of 1 with methyl isocyanate,[25] respectively, and the primary amide moiety remained. Over time, there have been suggestions that this amide is critical for anticancer activity. Such claims were supported by theoretical studies suggesting that a hydrogen bond donor at C8 is required for activity,[2,16] but clouding the picture is a conflicting structure-activity relationship (SAR) adopted from derivatives of a related compound (mitozolomide) in non-CNS cancer models.[26] There are considerable challenges to establishing a general synthetic route that can be used to construct novel derivatives at the C8 position; these synthetic challenges have hindered the development of new imidazotetrazines, and in the absence of new compounds and biological data, the outdated SAR has persisted.

Scheme 1.

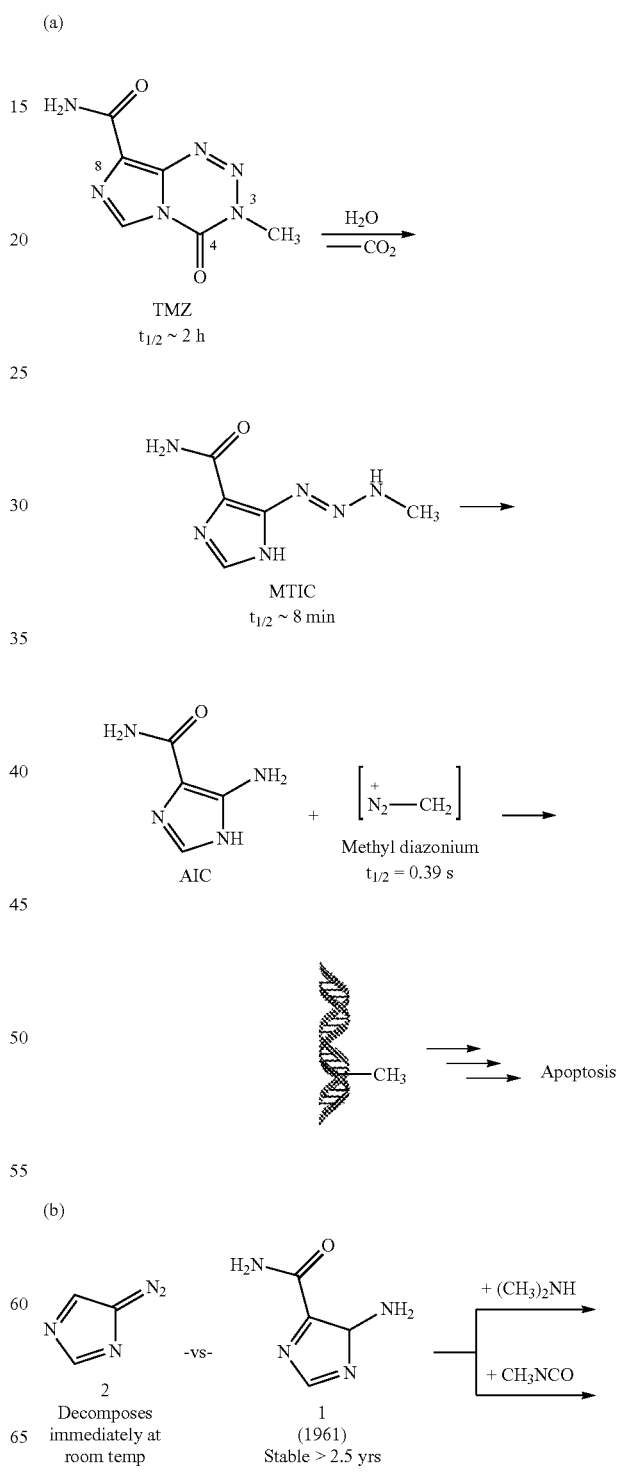

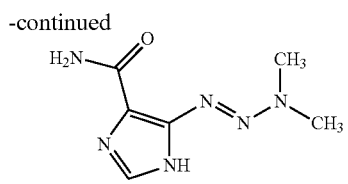

Imidazotriazene
Dacarbazine (1962)

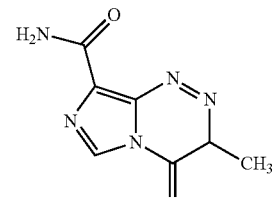

Imidazotetrazine
TMZ (1984)

(a) Mechanism of temozolomide (TMZ) activation in aqueous solution. (b) The favorable stability of compound 1 relative to related versions (such as 2) accounts for the incorporation of the amide at C8 of TMZ.

Challenges of replacing C8 amide include: aqueous sensitivity; base sensitivity; diazoimidazole degradation; and poor substitutes for $CH_3NCO$.

Key challenges to making novel imidazotetrazines include sensitivity to protic solvents or basic reagents, instability of intermediate diazo species, and the lack of efficient reagents to install the N3 methyl. The sensitivity of the prodrug to conditions involving base or water (at pH>6) renders the tetrazinone unstable to many practical cross-coupling or reducing conditions. Another challenge, as alluded to above, is the instability of intermediate diazo species. The privileged 4-diazoimidazole-5-carboxamide (1, Scheme 1b) readily precipitates out of solution as a pure, stable compound; however, other 4-diazoimidazoles (such as 2) remain in aqueous solution, are exceptionally prone to decomposition, and are sensitive to heat, shock, and often light.[23] Finally, installation of the N3-methyl group in the initial route to TMZ was achieved via cyclization with methyl isocyanate.[25] Methyl isocyanate, however, is a poisonous gas and no longer commercially available. As such, alternate routes[27] or less effective alternatives to methyl isocyanate such as N-succinimidyl N-methylcarbamate or N-methylcarbamic chloride must be used that reduce the yield of the cyclizations.

To provide access to certain derivatives of the C8 amide, an exploration of these types of compounds was begun by modifying an established route, largely developed for mitozolomide.[28] This sequence begins with a hydrolysis of the amide of TMZ to carboxylic acid 3 (Scheme 2a), which can then be converted to the acid chloride. From this intermediate, substitution with various nucleophiles provides products in high yields. This route was used to synthesize amide, ester, and thioester derivatives 4-10 (Scheme 2a). Additionally, an established reaction was employed to install a cyano group (11) directly from TMZ (Scheme 2a).[29] The creation of a structurally diverse panel of C8 analogs, however, would require novel synthetic routes, especially for those with aliphatic, ketone, halogen, and aryl groups; such substituents have not been described at this position in the ~35 year history of TMZ. Thus, an aliphatic group at C8 was introduced via diazotization of 5-amino-4-methylimidazole 12 to diazo species 13 and subsequent cyclization with methyl isocyanate surrogate N-methylcarbamoyl chloride to afford C8-methyl derivative 14 (Scheme 2b).

Although various amides, esters, and thioamides had been installed at C8, ketones were entirely absent, perhaps unsurprisingly since initial attempts to use Grignard or alkyllithium reagents led to complete degradation of the tetrazinone ring. Thus, a stepwise cyclization was utilized to synthesize methyl ketone derivative 17 from its disubstituted precursor 16, obtained upon hydrolytic degradation of 6-methylpurine N-oxide (15)[30] (Scheme 2c). Bromine and chlorine substituents were directly incorporated at C8 in moderate yields upon a decarboxylative halogenation of intermediate 3 employing Dess-Martin periodinane and the respective tetraethylammonium salt (compounds 18 and 19, Scheme 2a). This strategy had not previously been applied to imidazoles and endows potential points of diversity in addition to representing novel derivatives themselves. Using 18 as a cross coupling partner, however, was unsuccessful due to the basic, aqueous conditions required. Instead, a Suzuki coupling fashioned 5-nitro-4-phenylimidazole (21) from the 5-nitro-4-bromoimidazole (20) precursor, which could be subsequently reduced to corresponding amine 22 and cyclized to the phenyl-substituted imidazotetrazine as above (Scheme 2d). This method supplied 23 as well as a small series of p-substituted aryl derivatives 24-26. Finally, heterocyclic compounds 27 and 28 (Scheme 2e) were synthesized upon cyclization of the C8 amide or thioamide, respectively; an analogous route had been utilized to introduce bulkier 4-substituted oxazoles and thiazoles at the C8 position,[19] but not smaller methyl groups.

Figure 6:
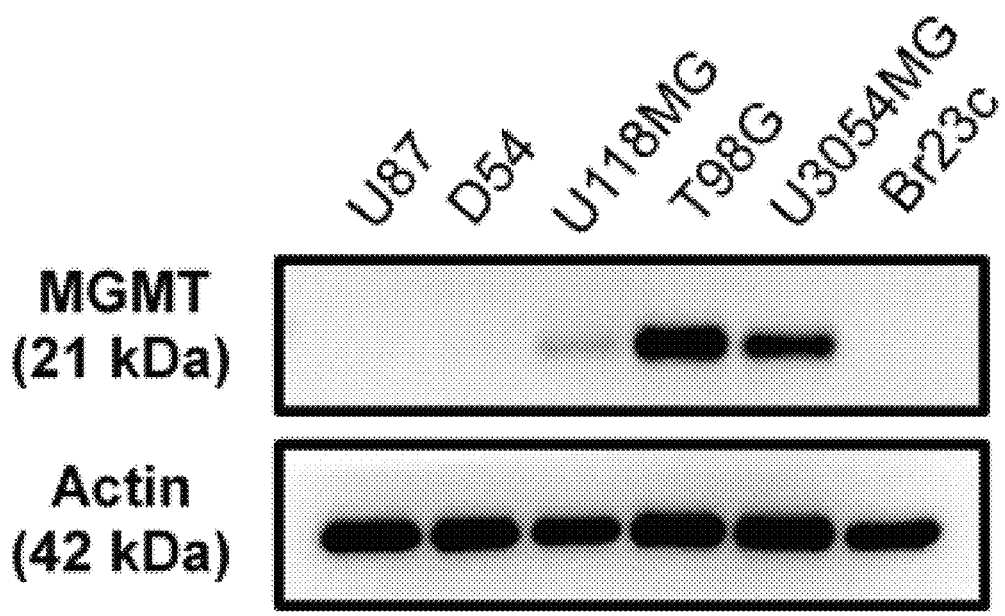
FIG. 6. Western blot for MGMT status of all cell lines used.

Anticancer activity of C8 substituted imidazotetrazines. With a suite of imidazotetrazines in hand, each compound was evaluated against a panel of human GBM cell lines (Table 1a, Table 1b). Cell lines were selected to include those expressing and lacking MGMT (FIG. 6) and, consistent with literature reports, those with negligible MGMT expression were sensitive to TMZ ($IC_{50}$~50 µM or less) whereas those with significant MGMT expression were resistant ($IC_{50}$>300 µM). Amide-substituted derivatives 4-8 as well as ester (9) and thioester (10) derivatives had activity comparable to TMZ in the MGMT-deficient U87 and D54 cell lines. Notably, the retention of activity for disubstituted amide (5-8) and ester (9) imidazotetrazines confirms that a hydrogen bond donor is not required at C8. In U118MG and T98G MGMT-expressing GBM cells, more potent activity was observed for these derivatives compared to TMZ.

Ketone analog 17 was also effective against MGMT-deficient cell lines, demonstrating that an amide is not required at the C8 position. Compounds completely lacking a carbonyl, such as 14, 19, 23, and 27 proved to be as (or more) potent than TMZ in the absence of MGMT and significantly more potent in cell lines expressing MGMT. Methyl (14) and phenyl (23) substitutions were the most active across all cell lines. Cyano derivative 11 and carboxylic acid derivative 3 were inactive in all tested cell lines (>7-fold less potent than TMZ), even in the absence of MGMT. In addition to these canonical adherent GBM cell lines, most analogs were more active than TMZ in the patient-derived U3054MG GBM cell line cultured under serum-free stem cell conditions.[31]

Scheme 2. Synthesis of novel C8-substituted imidazotetrazines.
a)
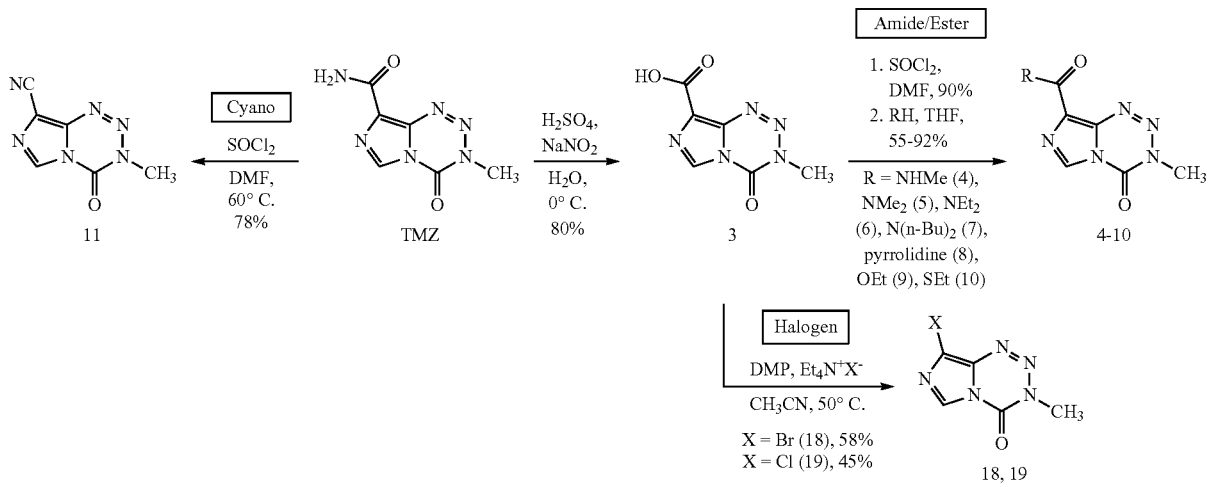
b) Aliphatic
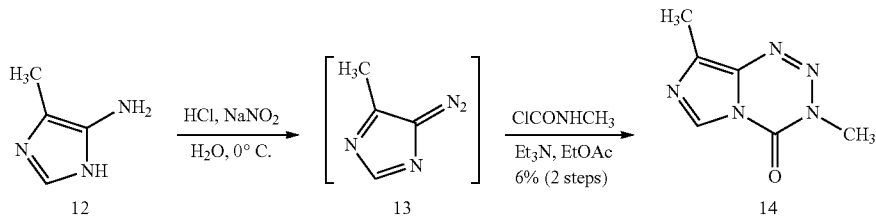
c) Ketone
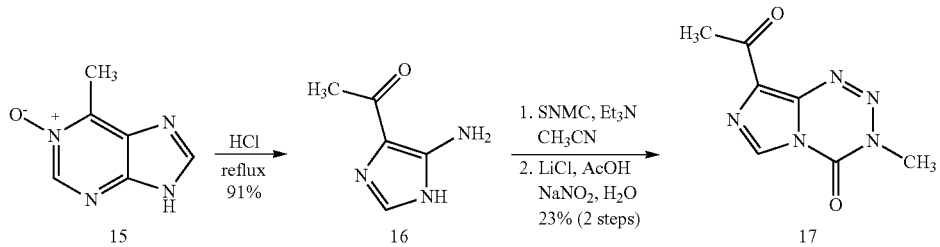
d) Aryl
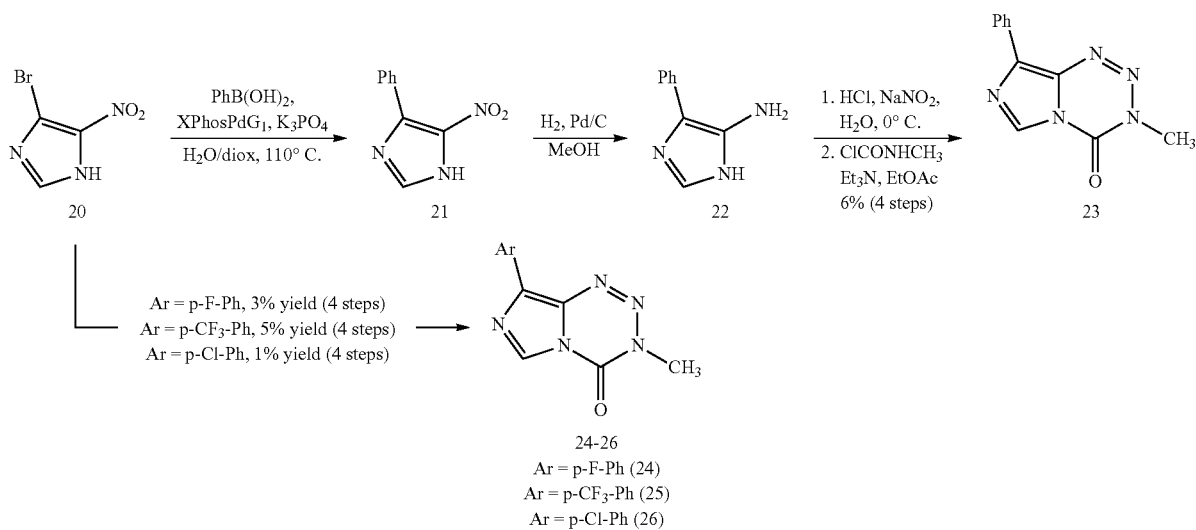

e) 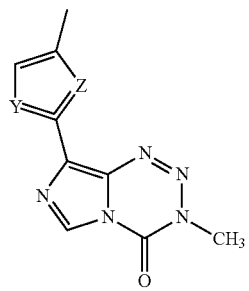

Y = N, Z = O (27), 12%
(4 steps from TMZ)
Y = S, Z = N (28), 21%
(2 steps from TMZ)

DMP = Dess-Martin periodinane, SNMC = N-succinimidyl N-methylcarbamate.

This disclosure therefore also provides methods for preparing compounds of the formulas described herein using the methods outlined in the schemes above, wherein any alkyl (e.g., methyl) or phenyl of the structures in the schemes can be replaced with other substituents, such as alkyl or phenyl groups, including substituted alkyl and/or phenyl groups. Substituents on the alkyl and/or phenyl groups can be one or more substituents as recited in the definition of a substituent above.

In various embodiments, the invention provides a method of preparing a substituted imidazotetrazine of a formula described herein comprising the steps outlined in Scheme 2 above, for example, the steps as substantially shown in part a), part b), part c), or part d) of Scheme 2, wherein any alkyl or phenyl group shown in the relevant scheme can be illustrated as a general R group that is defined as alkyl or phenyl, each optionally substituted and/or optionally unsaturated (for the alkyl). For example, C-8 substituted imidazotetrazines can be prepared by the method of Scheme 2, part b) wherein the methyl substituent of imidazole 12 is a different alkyl group, such as a $(C_2-C_{10})$alkyl, optionally branched and/or optionally substituted, and the N-methyl group of product 14 can have various alkyl or phenyl groups on the corresponding nitrogen in place of the methyl of that N-methyl group. Various alkynyl groups can be present in the final product, for example, at locations C-8 and/or N-2. Relevant imidazole starting materials can be purchased commercially or prepared by known methods. Numerous methods for preparing substituted imidazoles are well-known in the art.

TABLE 1a

Panel of C8-substituted imidazotetrazines and associated $IC_{50}$ values (μM) in multiple GBM cell lines. Cell lines were incubated with compound for 7 days then viability was assessed using the Alamar Blue assay. Error is SEM, n ≥ 3. Prl = pyrrolidine. A table with additional compounds (Table 1b) and a Western blot for MGMT status of all cell lines used (FIG. 6) are disclosed herein.

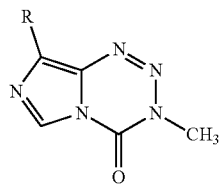

| | | | | MGMT | | |
|---|---|---|---|---|---|---|
| | | − | − | + | + | + |
| Compound | R | U87 | D54 | U118MG | T98G | U3054MG |
| TMZ | CONH$_2$ | 51 ± 8 | 12 ± 1 | 322 ± 7 | 660 ± 10 | 370 ± 40 |
| 3 | COO— | 320 ± 7 | 130 ± 8 | 370 ± 20 | 321 ± 8 | ND |
| 4 (Me-TMZ) | CONHMe | 49 ± 7 | 11 ± 1 | 280 ± 20 | 580 ± 20 | 290 ± 20 |
| 5 (DiMe-TMZ) | CONMe$_2$ | 40 ± 20 | 12 ± 5 | 130 ± 30 | 250 ± 60 | 132 ± 6 |
| 6 | CONEt$_2$ | 80 ± 30 | 13 ± 2 | 80 ± 10 | 160 ± 40 | ND |
| 7 | CON(n-Bu)$_2$ | 27 ± 6 | 11 ± 2 | 62 ± 2 | 140 ± 20 | ND |
| 8 | CO(Prl) | 17 ± 3 | 12 ± 4 | 136 ± 8 | 186 ± 5 | ND |
| 9 | COOEt | 66 ± 3 | 7 ± 1 | 180 ± 20 | 236 ± 10 | ND |
| 10 | COSEt | 64 ± 21 | 8 ± 1 | 165 ± 4 | 327 ± 4 | ND |
| 11 | CN | 500 ± 60 | 91 ± 6 | 670 ± 20 | >1000 | 870 ± 60 |
| 14 | Me | 3 ± 1 | 6 ± 3 | 7 ± 1 | 6 ± 1 | ND |
| 17 (K-TMZ) | COMe | 44 ± 6 | 18 ± 1 | 115 ± 9 | 240 ± 20 | 125 ± 4 |
| 19 | Cl | 15 ± 4 | 21 ± 4 | 60 ± 20 | 60 ± 10 | 87 ± 4 |
| 23 | Ph | 9 ± 1 | 7 ± 1 | 3 ± 1 | 14 ± 1 | 18 ± 1 |

TABLE 1a-continued

| | | | | | | |
|---|---|---|---|---|---|---|
| 27 (Ox-TMZ) | 5-Me-Oxaz | 27 ± 4 | 9 ± 1 | 70 ± 20 | 100 ± 20 | 123 ± 6 |
| 28 | 4-Me-Thiaz | 9 ± 1 | 8 ± 1 | 12 ± 2 | 31 ± 4 | ND |

Figure 7:
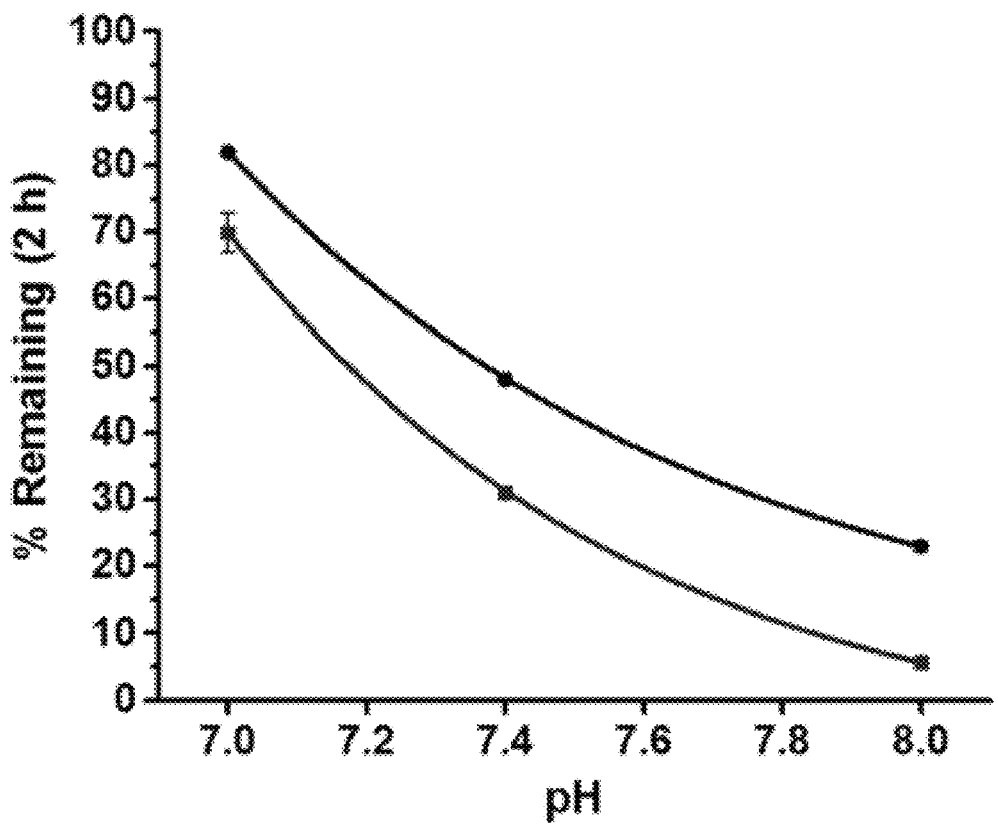
FIG. 7. The hydrolytic stabilities of TMZ and K-TMZ assessed in saline at pH 7.0, 7.4, and 8.0 by calculating the percentage of parent compound remaining after 2 h at 37° C.

Hydrolytic stability of C8 substituted imidazotetrazines. The principal aspect governing the anticancer activity of imidazotetrazines is the hydrolytic activation of the prodrug. As depicted in Scheme 1(a), TMZ has a half-life of ~2 hours in humans.[7] This timeline allows the intact prodrug to reach the brain and release the active methylating component prior to elimination. Beyond TMZ, the relationship between imidazotetrazine stability and anticancer activity is unknown; that is, while hydrolytic activation is required for cancer cell death, the optimal timing of this event is unclear both in vitro and in vivo. Towards this end, the hydrolytic stability of each new compound was assessed in buffered saline, which mimics in vivo conditions (in pH 7.4 PBS TMZ has a half-life of 119 minutes, FIG. 1). A HPLC assay was developed to quantify the fraction of intact prodrug remaining in solution after 2 hours at pH 7.4, 37° C. The results of this experiment suggest that electronic substituent effects at C8 directly translate through the bicycle to $C_4$, the site of hydrolysis. The magnitude of this effect was dramatic, with stabilities ranging from 0% to 97% remaining after 2 hours depending on the substituent at the C8 position (FIG. 1). Since the group at C8 appeared to have such a clear influence on the aqueous stability of the prodrug, its Hammett constant ($\sigma_p$) was plotted against the percent remaining after 2 hours. As shown in FIG. 1, an obvious relationship exists between these two parameters, suggesting that $\sigma_p$ can be used to accurately predict the stability of C8-substituted imidazotetrazines. Among those compounds possessing substituents with similar electronics ($0.23 < \sigma_p < 0.50$) to a primary amide ($\sigma_p = 0.36$) were amide derivatives 4 and 5, ketone derivative 17, and chloro derivative 19. Each had measured half-lives within an hour of TMZ in PBS at pH 7.4 (Table 1c). On either extreme were cyano analog 11 ($\sigma_p = 0.66$), with a half-life of 0.5 h, and methyl derivative 14 ($\sigma_p = -0.17$), which remained in its prodrug form the longest with a half-life of 40 hours. The same assay was used to confirm that hydrolysis remained pH-dependent for C8-substituted derivatives (e.g. K-TMZ 17, FIG. 7).

TABLE 1c

Half-lives of select C8 derivatives in PBS (pH 7.4, 37° C.).

| Compound | $t_{1/2}$ (h) |
|---|---|
| 11 | 0.57 ± 0.03 |
| 17 (K-TMZ) | 1.20 ± 0.10 |
| TMZ | 1.98 ± 0.01 |
| 4 (Me-TMZ) | 2.70 ± 0.10 |
| 5 (DiMe-TMZ) | 2.80 ± 0.20 |
| 25 | 2.90 ± 0.30 |
| 27 (Ox-TMZ) | 3.00 ± 0.10 |
| 19 | 3.10 ± 0.10 |
| 23 | 27 ± 3 |
| 14 | 40 ± 1 |

Relationship between hydrolytic stability and anticancer activity. Methyl and phenyl derivatives 14 and 23 were consistently the most potent compounds in each of the tested cell lines (Table 1a). Interestingly, they also possessed electron-donating substituents and, accordingly, the greatest aqueous stability (FIG. 1), suggesting that a longer-lived prodrug is favorable for efficacy in cell culture. The opposite effect was observed for compound 11, which was the least stable in solution. Even in U87 cells lacking MGMT, it exhibited a ten-fold loss of activity compared to TMZ, suggesting that there is a critical threshold of aqueous stability below which hydrolysis occurs too quickly to methylate target DNA. Compounds with hydrolytic stabilities similar to TMZ such as 4, 5, 17, 19, and 27 retained activity in culture. Notably, ketone derivative 17 was equipotent to TMZ even with a shorter aqueous half-life, indicating that compounds with $\sigma_p \sim 0.50$ can still retain marked anticancer activity.

Liver microsome stability. TMZ fortuitously possesses several ideal pharmacokinetic properties including avoidance of primary metabolism.[7] To assess whether modification or replacement of the amide at C8 would lead to TABLE 1b Panel of C8-substituted imidazotetrazines and associated 7-day $IC_{50}$ values (μM) in multiple GBM cell lines; the four compounds below were tested, and this supporting table is a complement to Table 1a. Cell viability was assessed using the Alamar Blue assay. Error is SEM, n ≥ 3.

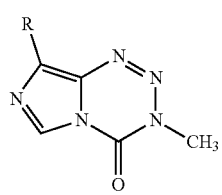

| | | MGMT | | | |
|---|---|---|---|---|---|
| | | − | − | + | + |
| Compound | R | U87 | D54 | U118MG | T98G |
| TMZ | $CONH_2$ | 51 ± 8 | 12 ± 1 | 322 ± 7 | 660 ± 10 |
| 18 | Br | 26 ± 7 | 20 ± 1 | 80 ± 20 | 60 ± 10 |
| 24 | $C_6H_4$-4-F | 13 ± 2 | ND | ND | 18 ± 2 |
| 25 | $C_6H_4$-4-$CF_3$ | 16 ± 1 | ND | ND | >100 |
| 26 | $C_6H_4$-4-Cl | 9 ± 1 | 7 ± 1 | 5 ± 1 | 19 ± 3 | significant metabolic liabilities, the stabilities of select compounds were assessed after 2 hours in the presence of mouse liver microsomes. Prodrug hydrolysis was accounted for by including control runs that did not contain liver microsomes. The slightly acidic pH of the working solution resulted in enhanced stability of TMZ compared to incubation in PBS alone. Predictably, TMZ was insensitive to metabolic perturbation as its instability was entirely accounted for by hydrolysis (Table 2a). The addition of methyl(s) to the amide (compounds 4 and 5) resulted in some susceptibility to the effects of the microsomes, and this effect was amplified for larger amide substitutions (compound 7), which demonstrated improved aqueous stability but markedly less stability in liver microsomes. Ketone 17 and chloro 19 were generally stable to oxidative metabolism, suggesting that for these compounds the hydrolysis could drive the pharmacokinetics in vivo, similar to TMZ.

Blood-brain barrier penetrance. It has been reported that >98% of small molecule drugs do not penetrate the BBB,[32] making TMZ unusual, especially amongst anticancer agents. In humans, TMZ is rapidly absorbed and reaches the brain in minutes with cerebral spinal fluid concentrations averaging 20% of those in the plasma;[8,9] the accumulation of even more drug in the brain by increasing the BBB penetrance may be a viable strategy to increase efficacy against CNS-based tumors. To predict the BBB penetrance of the novel imidazotetrazines, log BB values were calculated (c Log BB) based on a formula utilizing c Log P and total polar surface area.[33] When applied across a consistent drug scaffold, these types of in silico metrics have been used reliably to predict relative changes in BBB penetrance as well as other biological phenomenon,[34-38] though not always reflective of absolute concentrations. The c Log BB value for TMZ is −1.58 (Table 2a). Replacing the primary amide led to marked increases in the c Log BB and larger predicted brain:blood ratios relative to TMZ. Importantly, c Log BB does not account for molecular weight, making one wary of analogs with large, hydrophobic functionality (e.g. 7) even if they possess attractive predicted values. A more comprehensive metric, the CNS multiparameter optimization (MPO) tool[39,40] was also employed to gauge prospective BBB permeabilities. CNS MPO scores span from 0 to 6.0 based on the optimal ranges of 6 physicochemical properties. Though TMZ has an agreeable MPO of 4.9, higher scores were achieved for the C8 analogs, which in several cases reached the top desirability value (Table 2a). The more favorable c Log BB and CNS MPO values predicted for the panel suggests that certain derivatives may achieve higher drug concentrations in the brain than TMZ.

Figure 2:
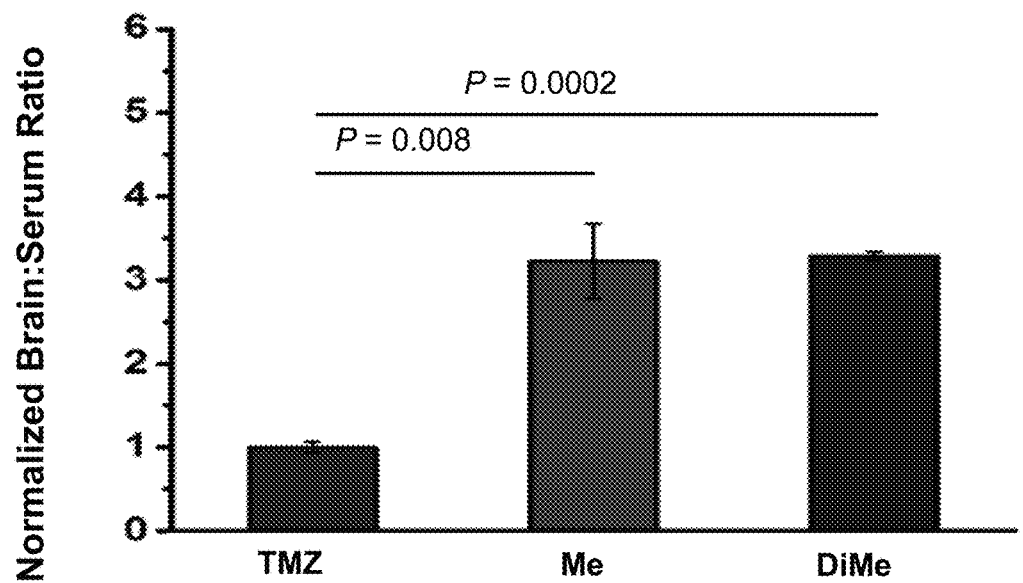
FIG. 2. (a) Relevant brain:serum ratios of TMZ, Me-TMZ, and DiMe-TMZ (25 mg/kg) were measured 5 minutes after IV injection into mice. Values are the fold change of brain:serum ratio relative to TMZ. In a second experiment, brain (b) and serum (c) concentrations of TMZ and C8 analogs (25 mg/kg) were quantitated 5 minutes after IV injection into mice. (d) Brain:serum ratios were calculated based on (b) and (c) assuming a mouse blood volume of 58.5 mL/kg (see Scheme 2b). Error is SEM, number of mice per cohort=3. Statistical significance was determined by using a two-sample Student's t-test (two-tailed test, assuming equal variance).
Figure 2:
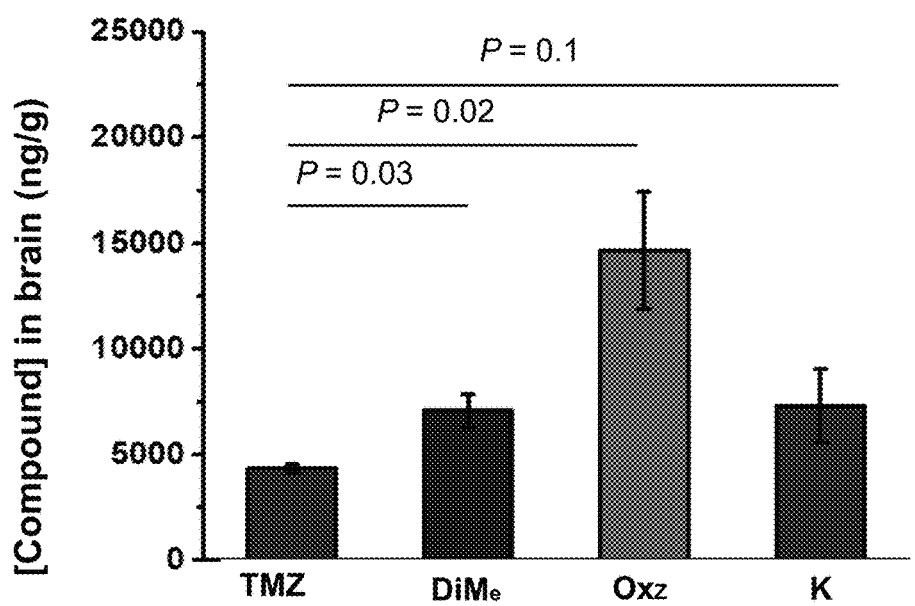
Figure 2:
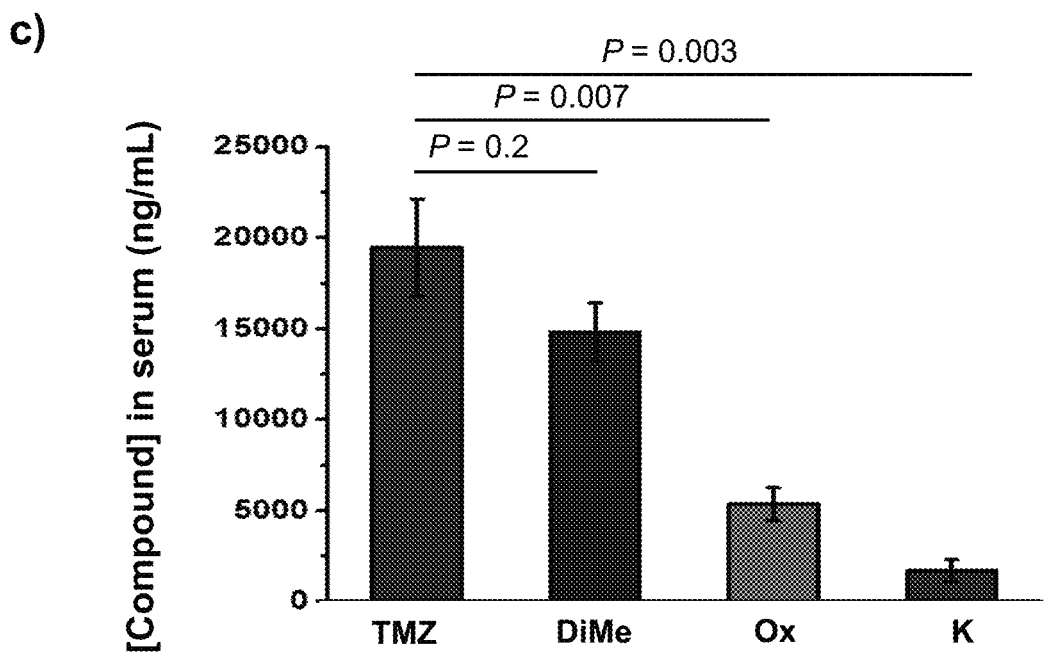
Figure 2:
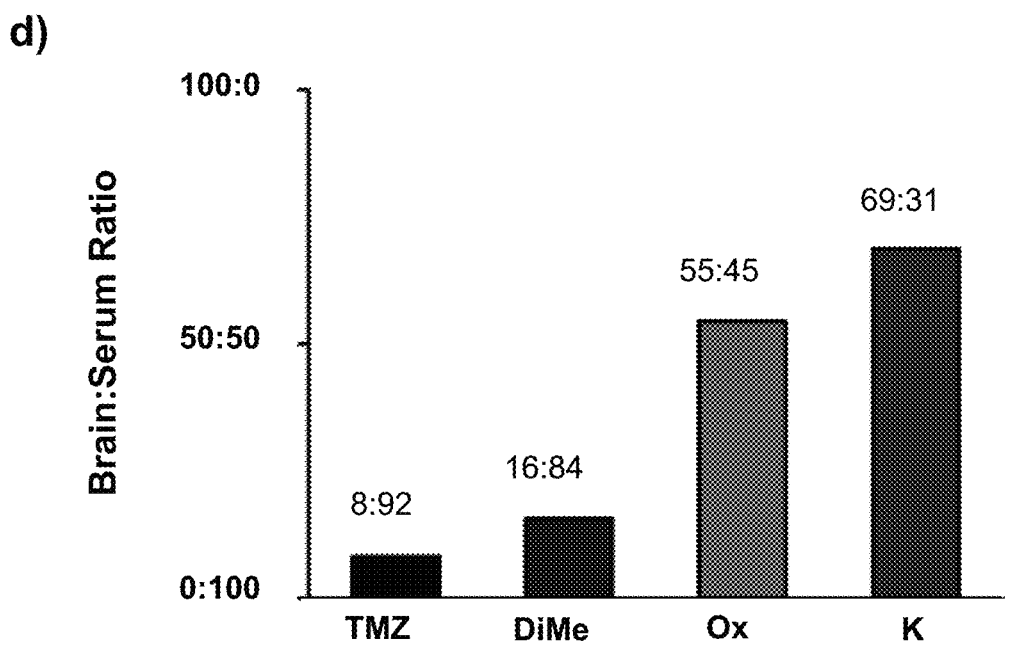

The BBB penetrance of top compounds (those with favorable anticancer activity, appropriate hydrolytic and liver microsome stability, and predicted BBB penetrance, Scheme 2b) was thus assessed in vivo. In an initial experiment, Me-TMZ (4) and DiMe-TMZ (5) were tested head-to-head with TMZ to explore whether alkylation of the C8 amide could confer increased brain:blood ratios. Mice were administered 25 mg/kg drug intravenously and sacrificed 5 minutes after injection. The serum and perfused brain samples were immediately acidified to prevent prodrug degradation before the drug concentration within each compartment was quantitated by LC-MS/MS. After 5 minutes, drug concentrations in the brain were significantly elevated for analogs Me-TMZ and DiMe-TMZ versus TMZ, a >3-fold increase in brain:serum ratio for each compound (FIG. 2a). The equivalent brain:serum ratios for Me-TMZ and DiMe-TMZ is likely due to the fast metabolism of the dimethylated amide to its monomethylated counterpart. This preliminary experiment suggested that other derivatives with higher predicted BBB penetrance may lead to greater brain permeability in vivo. Accordingly, compounds Ox-TMZ (27) and K-TMZ (17) were evaluated head-to-head with DiMe-TMZ and TMZ. After 5 minutes, each derivative had accumulated numerically higher concentrations in the brain than TMZ (FIG. 2b). When paired with the corresponding serum concentrations (FIG. 2c), TMZ had a relative brain:serum ratio of 0.23±0.03 ng/g:ng/mL, comparable to the few other TMZ biodistribution experiments in murine systems.[41,42] Assigning average mouse blood volumes to equate units, TMZ had an absolute brain:serum ratio of 8:92, while Ox-TMZ and K-TMZ boasted brain:serum ratios of 55:45 and 69:31, respectively. (FIG. 2d). The dramatic differences in drug partitioning suggest that replacing the amide at C8 is a viable strategy to significantly increase local drug concentration in the brain relative to the blood, which may increase effectiveness against brain tumors and also reduce hematological toxicity.

Scheme 2b. Structures of lead C8-substituted compounds. Blood-brain barrier permeability of imidazotetrazines (see FIG 2).

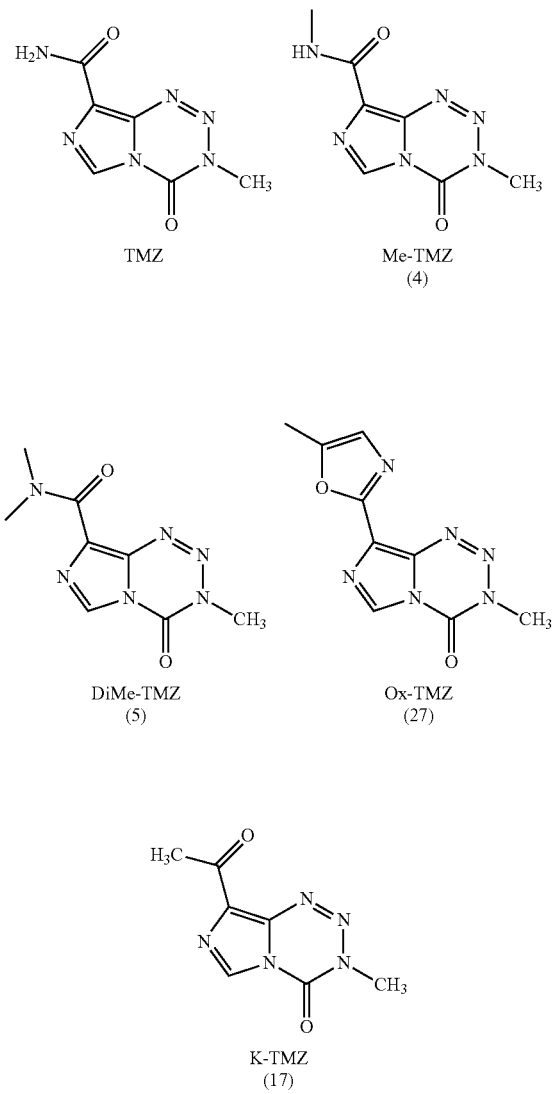

TABLE 2a

Metabolic stability, cLogBB, and CNS MPO values for relevant C8 analogs. The metabolic stability was assessed in mouse liver microsomes. Compounds were incubated in microsomes for 2 h, then the percentage remaining was quantified relative to t0. Experiments assessing stability in the absence of microsomes were identical but replaced liver microsomes with PBS. Error is SEM, n ≥ 2. Internal standard = N3-propyl TMZ. CNS MPO = Central Nervous System Multiparameter Optimization Score.

| Compound | Stability (2 h, Microsomes) | Stability (2 h, No Microsomes) | cLogBB | CNS MPO |
|---|---|---|---|---|
| Propranolol | 68 ± 2% | 102 ± 3% | ND | ND |
| TMZ | 87 ± 6% | 86 ± 4% | −1.58 | 4.9 |
| 4 (Me-TMZ) | 86 ± 1% | 93 ± 1% | −1.34 | 5.7 |
| 5 (DiMe-TMZ) | 81 ± 2% | 92 ± 3% | −1.18 | 6.0 |
| 6 | 81 ± 1% | 95 ± 2% | −1.07 | 6.0 |
| 7 | 1 ± 1% | 98 ± 3% | −0.78 | 5.6 |
| 17 (K-TMZ) | 70 ± 1% | 77 ± 3% | −1.08 | 6.0 |
| 19 | 91 ± 3% | 91 ± 1% | −0.72 | 6.0 |
| 23 | 44 ± 2% | 103 ± 5% | −0.56 | 5.7 |
| 27 (Ox-TMZ) | 71 ± 1% | 95 ± 4% | −1.19 | 5.9 |

Figure 3:
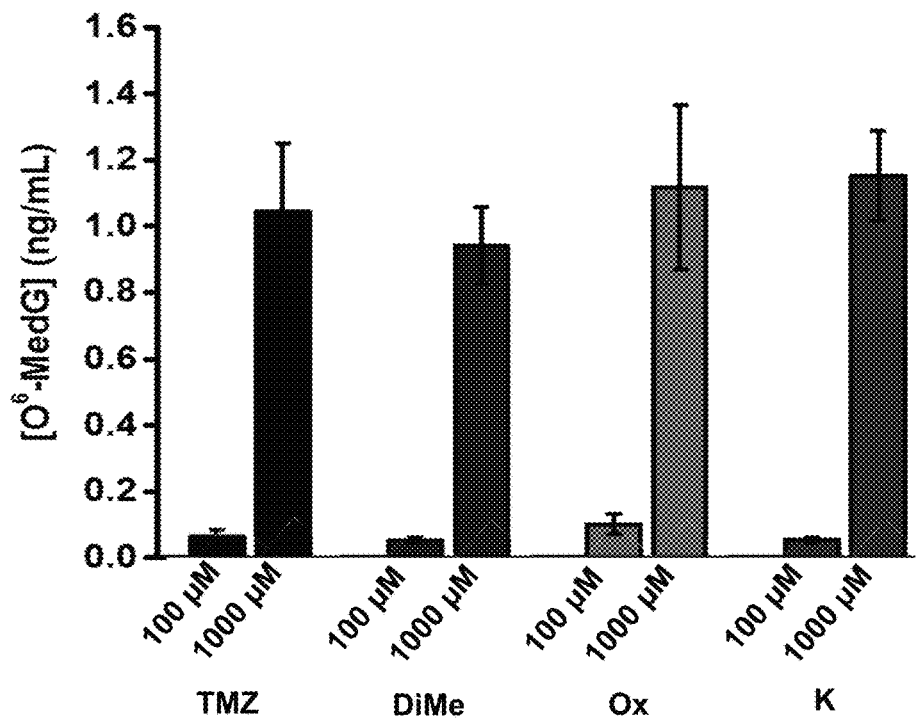
FIG. 3. Assessment of the hematological toxicity of imidazotetrazines in vivo. Mice were administered a single IV dose of 125 mg/kg imidazotetrazine. After 7 days, whole blood was collected, and a complete blood count was obtained for each individual mouse. (a) Total WBC count. Control vs. Ox-TMZ: P=0.7, Control vs. K-TMZ: P=0.9. (b) Lymphocyte concentrations. Control vs. Ox-TMZ: P=0.5, Control vs. K-TMZ: P=0.9. Error is SEM, number of mice per cohort=4. Statistical significance was determined by using a two-sample Student's t-test (two-tailed test, assuming equal variance). The concentrations of other relevant blood constituents are shown in FIG. 8.
Figure 3:
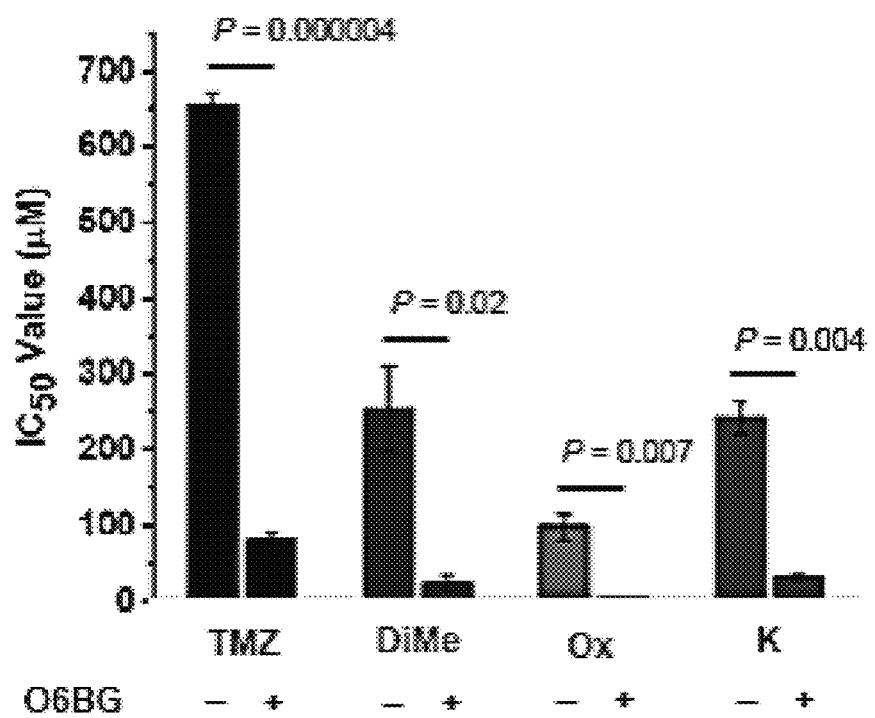
Figure 8A:
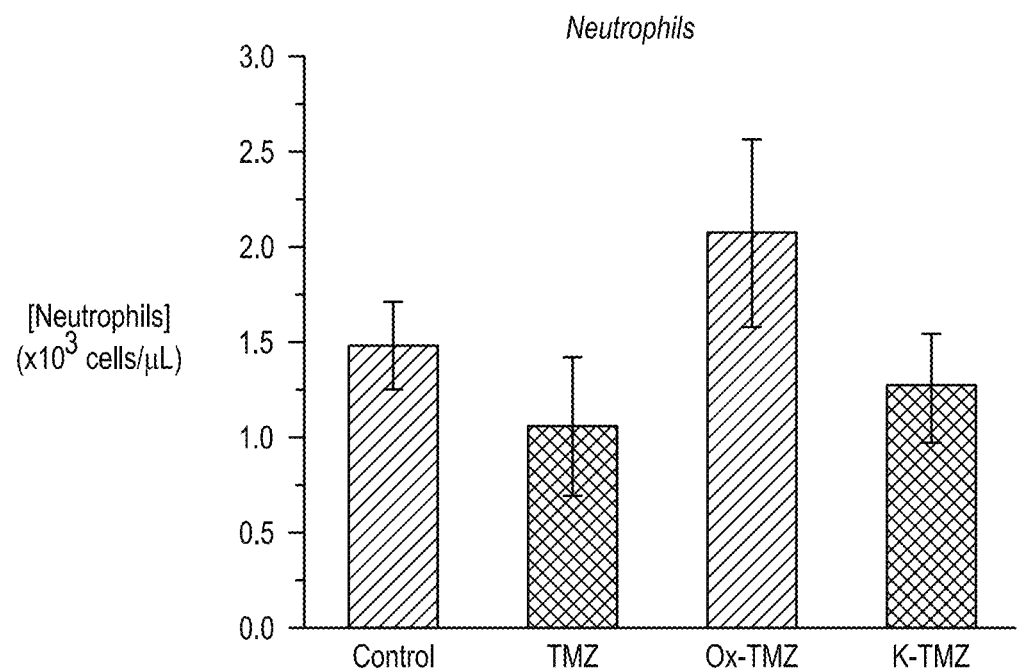
FIG. 8A-C. Assessment of the hematological toxicity of imidazotetrazines in vivo. Mice were treated with a single IV dose of 125 mg/kg imidazotetrazine and a complete blood count was obtained for each mouse after 7 days. (a) Neutrophil concentrations (b) RBC concentrations (c) Platelet concentrations (see Table 2b).
Figure 8B:
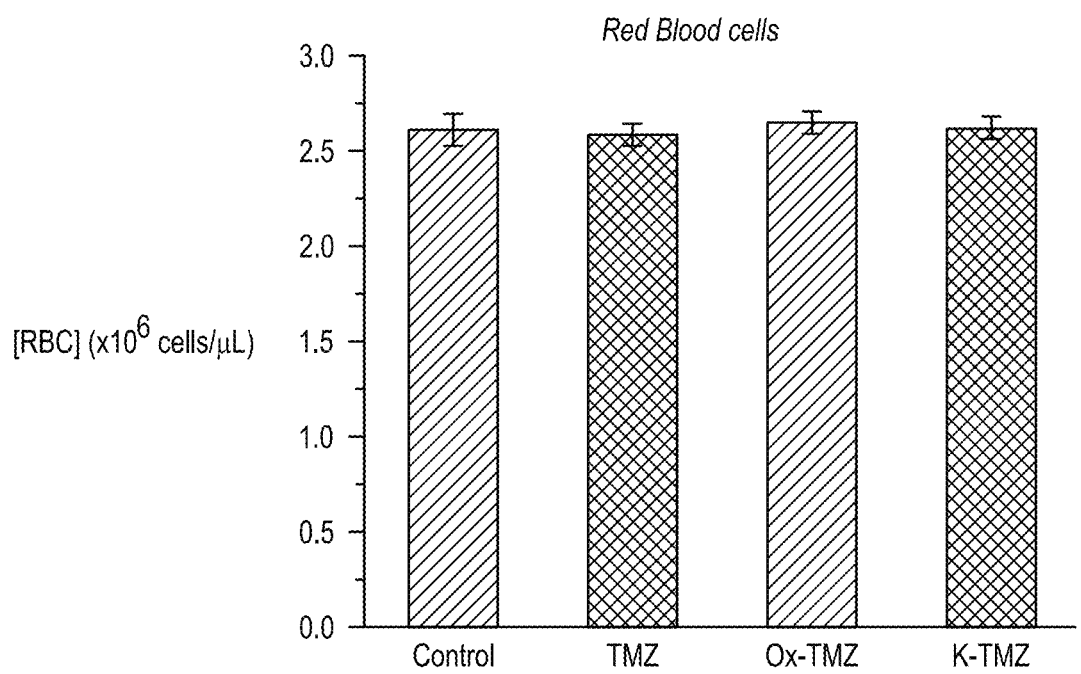
Figure 8C:
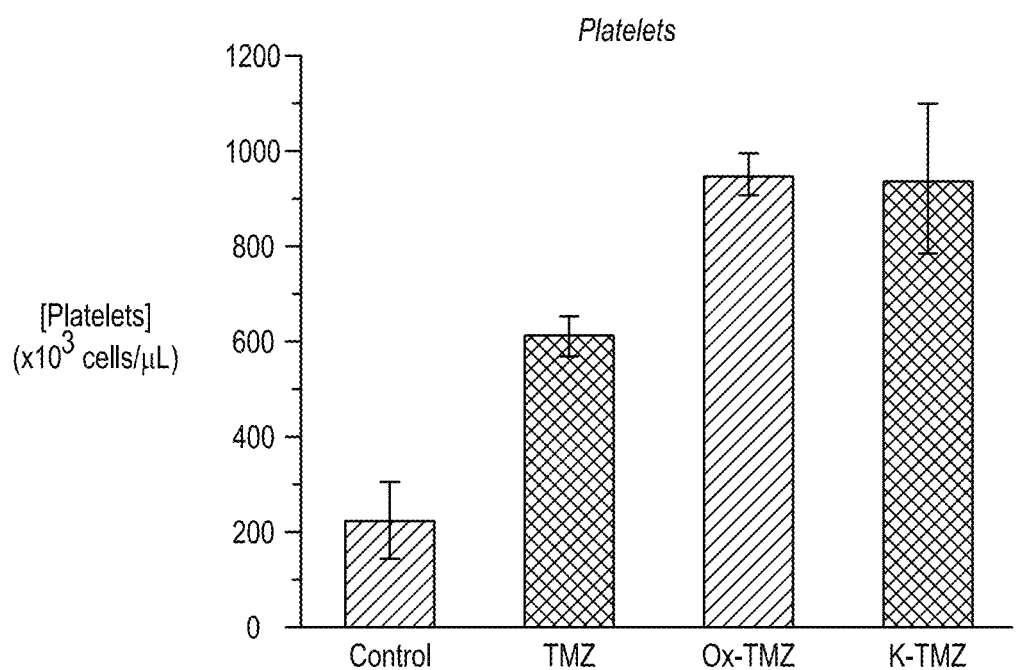

Assessment of hematological toxicity. The elevated brain concentrations and dramatically decreased serum concentrations (FIG. 2b, FIG. 2c) observed upon treatment with Ox-TMZ and K-TMZ compared to TMZ indicated that these C8-modified imidazotetrazines attenuate the dose-limiting hematological toxicity observed for TMZ in the clinic. To test this hypothesis, mice were treated with a single dose of 125 mg/kg TMZ, Ox-TMZ, or K-TMZ intravenously; this dose of TMZ induces non-lethal toxicity in mice.[43,44] Seven days post-treatment, whole blood was collected and complete blood counts were obtained for each individual mouse. Expectedly, a dose of 125 mg/kg TMZ led to white blood cell (WBC) depletion relative to control mice (FIG. 3a), suggestive of drug-induced myelosuppression. Both lymphocyte (FIG. 3b) and neutrophil (FIG. 8a) concentrations were decreased in TMZ-treated mice. Conversely, treatment with 125 mg/kg of Ox-TMZ or K-TMZ did not produce myelosuppression. Total WBC, lymphocyte, and neutrophil counts for mice treated with these compounds were equivalent to those of control mice. Notably, the novel imidazotetrazines did not give rise to other hematological symptoms such as red blood cell (RBC) toxicity (FIG. 8b) or thrombocytopenia (FIG. 8c) and did not lead to weight loss 7 days post-treatment (Table 2b).

TABLE 2b

Cohort weights of mice prior to treatment and at the time of blood collection 7 days post-treatment. Error is SEM, number of mice per cohort = 4 (see FIG. 8).

| Compound | Pre-treatment (g) | 7 days Post (g) |
|---|---|---|
| Control | 31 ± 1 | 32 ± 1 |
| TMZ | 31 ± 1 | 32 ± 1 |
| K-TMZ | 30 ± 1 | 31 ± 1 |
| Ox-TMZ | 30.7 ± 0.1 | 31.6 ± 0.3 |

Figure 4:
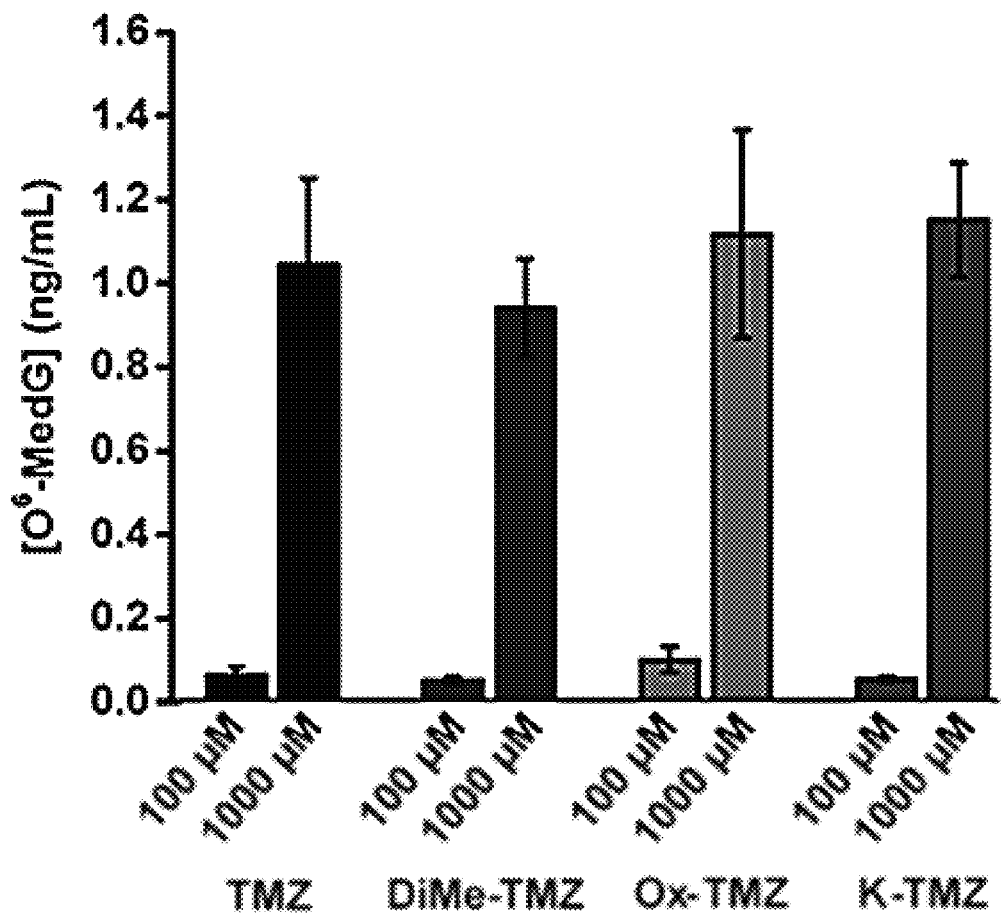
FIG. 4. Imidazotetrazines were added to T98G cells with or without 3 h pre-treatment of O6BG (100 μM). IC50 values after 7-day incubation and fold changes between (+/−) O6BG treatments are reported. P-values between IC50 values (+/−) O6BG<0.02 for all compounds. Error is SEM, n≥3. Statistical significance was determined by using a two-sample Student's t-test (two-tailed test, assuming equal variance).

Novel imidazotetrazines induce alkylation-mediated cancer cell death. The cytotoxicity of TMZ is mediated by methylation of $O^6$ guanine; subsequent single- and double-strand breaks and apoptosis are facilitated by the mismatch repair system.[2-6] To assess if the novel imidazotetrazines kill through the same mechanism, $O^6$-methylguanine adducts were quantitated in U87 cells treated with 100 or 1000 μM of each imidazotetrazine. After 8 hours of incubation with compound, the genomic DNA was isolated, quantified, and hydrolyzed to its constituent deoxyribonucleosides, which were quantitated via LC-MS/MS analysis. Dose dependent increases in the concentration of $O^6$-methylated deoxyguanosine were observed for TMZ as well as each of the lead compounds (Table 2c), indicating that DNA methylation is occurring. Further confirmation that the novel compounds remain DNA alkylators was obtained upon pre-treatment with MGMT inhibitor $O^6$-benzylguanine (O6BG). O6BG is a pseudosubstrate for MGMT that quenches cellular stores of the enzyme, leading to the persistence of $O^6$-methylguanine DNA adducts. Pre-incubation of MGMT-expressing T98G cells with O6BG (100 μM) led to an eight-fold enhancement in cytotoxicity for TMZ (FIG. 4), consistent with literature reports.[45,46] Similarly, DiMe-TMZ, Ox-TMZ, and K-TMZ demonstrated a significant increase in activity when administered after O6BG, suggesting that $O^6$-methylguanine lesions are the cause of cell death.

Figure 5:
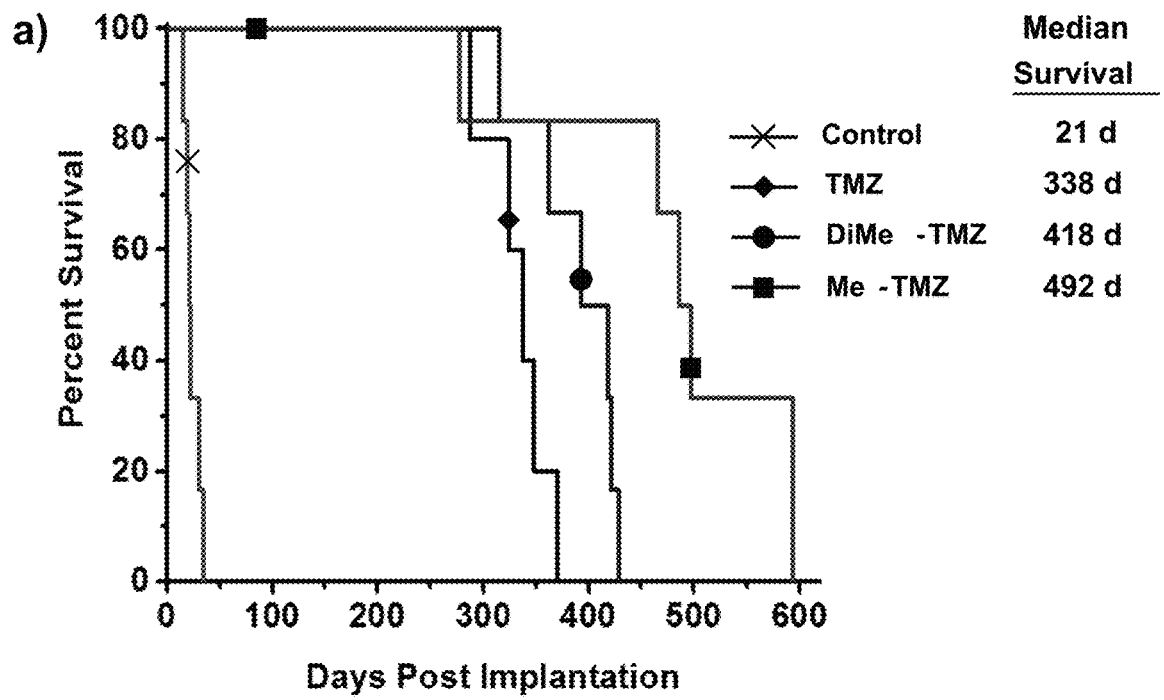
FIG. 5. Evaluation of imidazotetrazines in intracranial mouse models of GBM. GBM Br23c oncospheres were intracranially implanted into female athymic nude mice. Treatment was started 5 days post implantation. (a) Mice were administered 15 mg/kg TMZ or an equimolar dose of Me-TMZ (16.1 mg/kg) or DiMe-TMZ (17.2 mg/kg) orally once-per-day, 5x/week for 7 weeks. Control vs. TMZ: P=0.0014, TMZ vs. DiMe-TMZ: P=0.061, TMZ vs. Me-TMZ: P=0.016. (b) Mice were administered 15 mg/kg TMZ or an equimolar dose of DiMe-TMZ (17.2 mg/kg) or K-TMZ (14.9 mg/kg) orally once-per-day for 5 total doses. Control vs. TMZ: P=0.0007, DiMe-TMZ vs. TMZ: P=0.7, K-TMZ vs. TMZ: P=0.055. Compounds were formulated in 10% PEG in PBS immediately prior to each treatment. Number of mice per treatment cohort≥5. Survival curves were compared using log-rank test.
Figure 5:
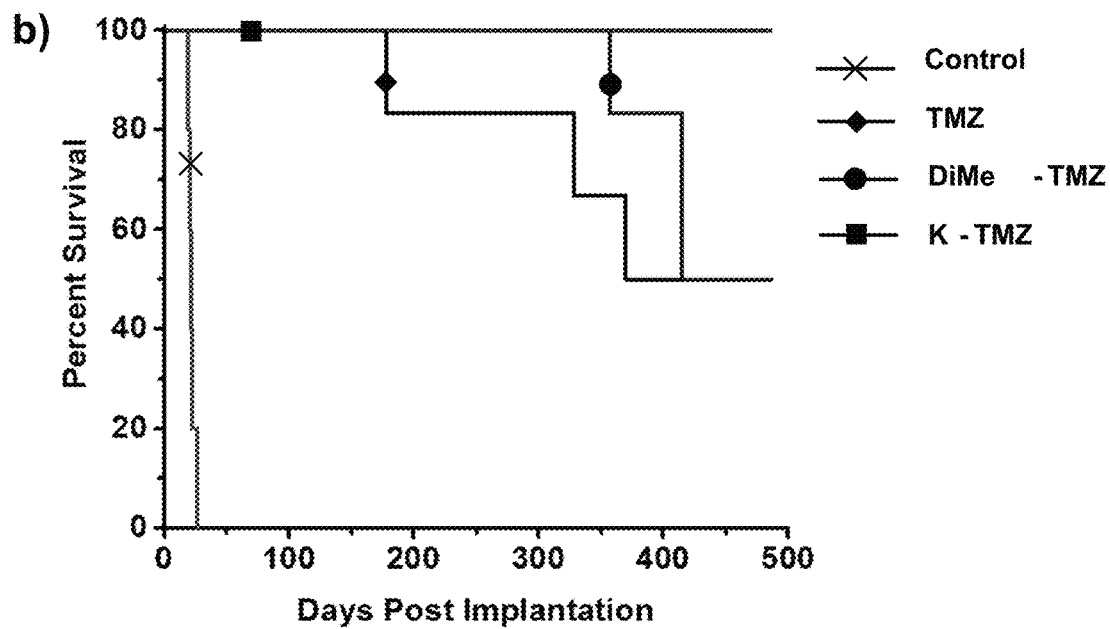
Figure 9:
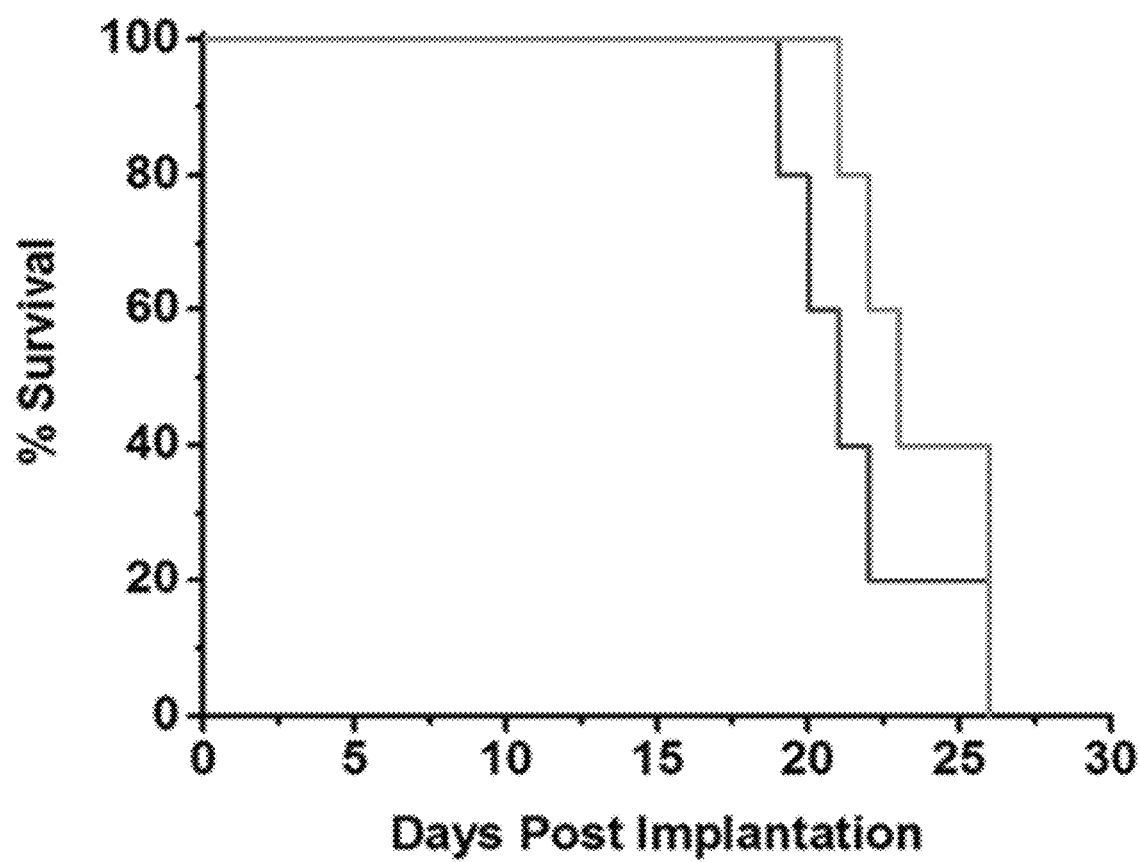
FIG. 9. GBM oncosphere Br23c cells were intracranially implanted into female athymic nude mice. Treatment was started 5 days post implantation. Mice were administered compound 14 (12.8 mg/kg, equimolar to 15 mg/kg TMZ) orally once-per-day for 5 doses. Compound was formulated in 10% PEG in PBS. n≥5. This experiment was run alongside that presented in FIG. 5b; the control group is the same for FIG. 5b and FIG. 9.
Figure 10:
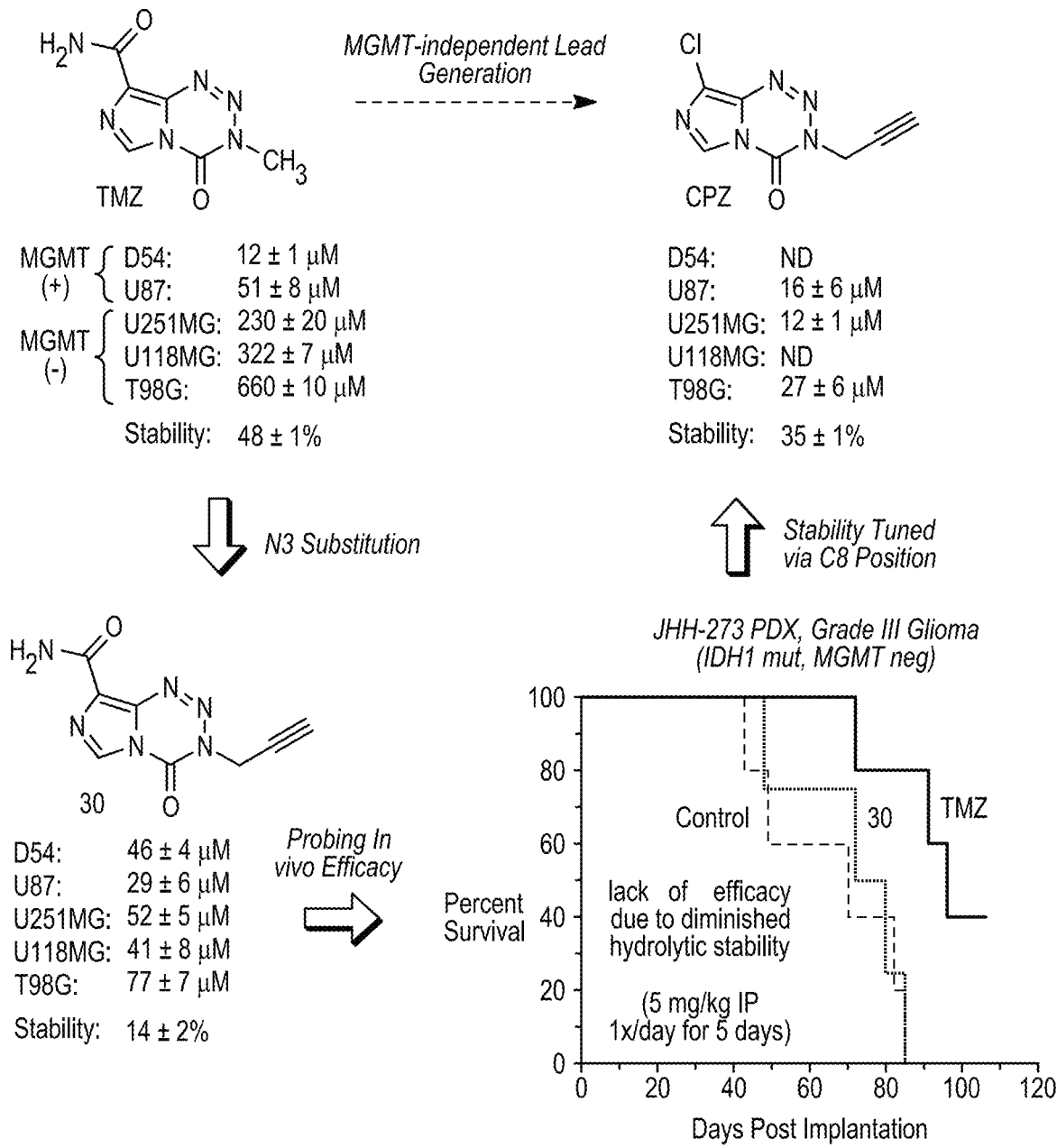
FIG. 10. Development pathway of MGMT-Independent Imidazotetrazines. Graph of brain:serum ratio: mice were administered 25 mg/kg compound IV. After 15 min, mice were sacrificed, and blood and brain were collected. The concentration of drug in each was quantified by LC-MS/MS. N≥3 mice per cohort, error is SEM. *P<0.05, **P<0.01.
Figure 10:
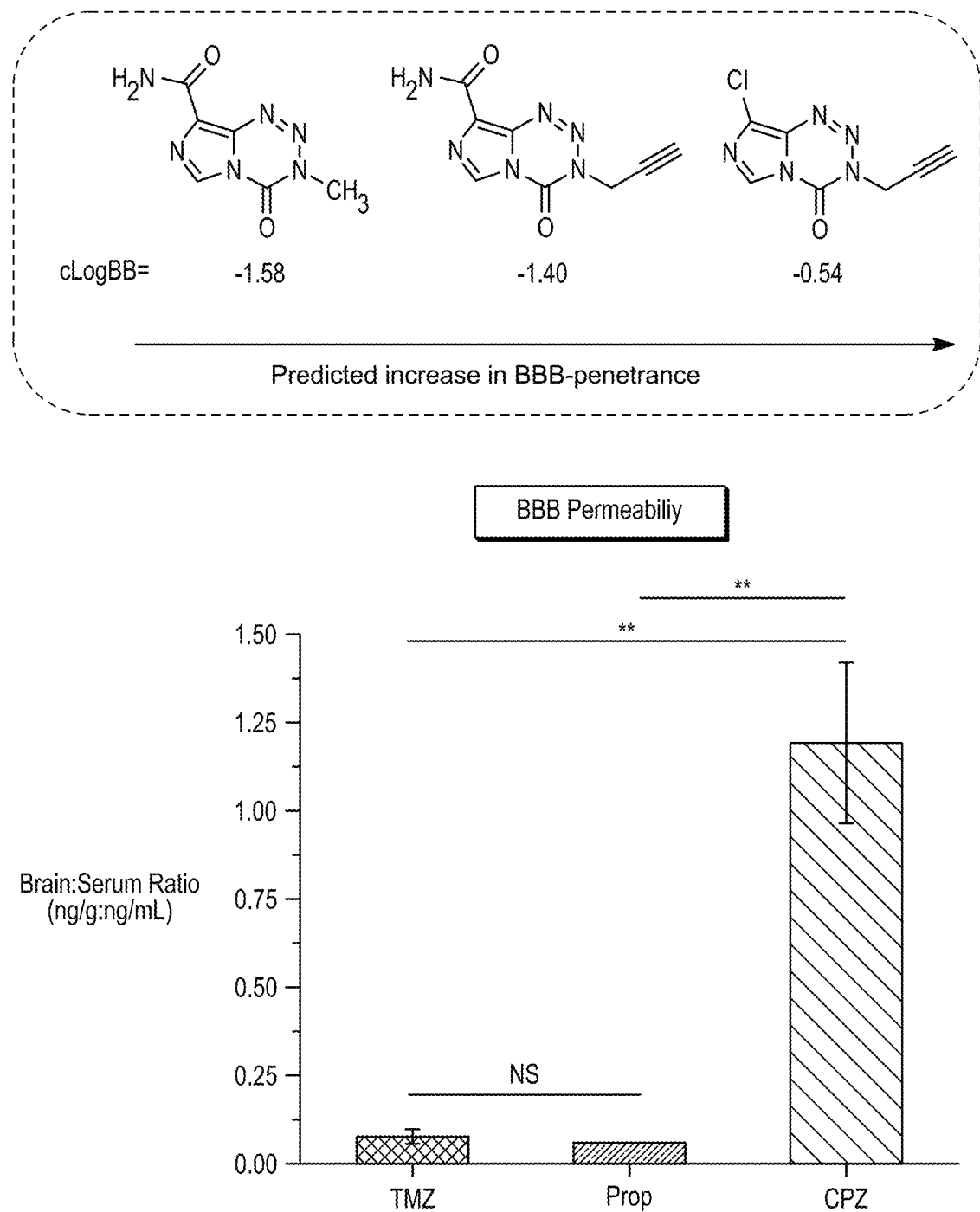

Novel imidazotetrazines have superior activity in mouse models of GBM. The increased BBB penetrance observed for amide derivatives (Me-TMZ and DiMe-TMZ) relative to TMZ suggested that greater drug concentrations in the brain might lead to greater efficacy in an intracranial tumor model. GBM oncosphere lines were chosen for these studies as they more accurately recapitulate the genetic and histopathological features of human GBM than traditional adherent cell lines, which are passaged in serum and typically grow as compact masses in vivo.[47] The Br23c GBM oncosphere cell line does not express MGMT, was sensitive to TMZ and the novel C8-substituted imidazotetrazines (Table 2d), and was thus chosen as the model system. Mice implanted intracranially with these cells were administered 15 mg/kg TMZ or the equimolar equivalent of Me-TMZ or DiMe-TMZ once-per-day, 5×/week via oral gavage. As expected, TMZ significantly increased median survival compared with vehicle (FIG. 5a). Mice treated with both Me-TMZ and DiMe-TMZ, however, outperformed TMZ and increased median survival by 24% and 46%, respectively, suggesting that increasing the BBB-permeability of imidazotetrazine prodrugs is a viable strategy to improve efficacy. In a second experiment, K-TMZ was selected for evaluation due to its most favorable brain:blood ratio (FIG. 2d). Mice intracranially implanted with Br23c cells were treated with K-TMZ (via oral gavage), which led to an extended median survival of more than 50 days past TMZ-treated mice, and showed greater efficacy even compared to DiMe-TMZ (FIG. 5b). Importantly, methyl derivative 14, which has excellent efficacy in cell culture but an extended (40 hour) half-life in aqueous solution, had no effect in this in vivo model (FIG. 9) suggesting that dramatically elongated half-lives are detrimental in vivo, likely due to compound clearance prior to hydrolytic activation.

TABLE 2c

The concentration of $O^6$-methylguanine was measured in U87 cells (10 μg DNA) after treatment with 100 or 1000 μM of imidazotetrazine for 8 hours.
$IC_{50}$ Values (μM)

| Compound | (−) O6BG | (+) O6BG | Fold Change |
|---|---|---|---|
| TMZ | 660 ± 10 | 81 ± 8 | 8 |
| DiMe-TMZ | 250 ± 60 | 25 ± 9 | 10 |
| Ox-TMZ | 100 ± 20 | 5 ± 1 | 20 |
| K-TMZ | 240 ± 20 | 32 ± 4 | 8 |

Conclusion. Despite being known since 1984, FDA approved since 1999, and reaching $1 billion in sales in 2009, TMZ remains the only approved imidazotetrazine anticancer drug; this likely stems from the lack of generalized syntheses for this class of compounds prohibiting conventional medicinal chemistry campaigns. Herein is reported new synthetic methods that enable the construction of novel C8-substituted imidazotetrazines that were previously inaccessible. Evaluation of these compounds in systematic, head-to-head assays led to the definitive conclusion that the C8 amide is not required for anticancer activity, and indeed compounds lacking an H-bond donor or acceptor (or both) at C8 can still retain activity comparable to TMZ against cancer cells in culture. Unmoored from the necessity of an amide at C8, a panel of imidazotetrazines was synthesized, varying this position. Strikingly, the electronic properties of the substituent at C8 has a dramatic effect on the activation of the corresponding prodrug, a previously undefined phenomenon. The relationship derived herein between the hydrolytic stability of imidazotetrazines and the electronics at C8 allows the stability of the prodrug to be tuned by employing easily accessible $\sigma_p$ values, enabling the rational design of TMZ derivatives that have similar stabilities in vivo and facilitating investigation into the optimal timing of imidazotetrazine prodrug activation.

From this work it appears that compounds with very short half-lives (such as 11, $t_{1/2}$=0.57 h) simply hydrolyze too rapidly, releasing methyl diazonium prior to accumulation in the DNA microenvironment and diminishing anticancer activity. Thus, for activity against cancer cells in culture, a half-life of 1 h or greater is optimal. Conversely, compounds that have very long half-lives (such as 14 or 23, $t_{1/2}$>20 h) can be distinctly more potent than TMZ in cell culture as the prodrug has ample time to distribute to the nucleus before conversion to the active methylating agent. However, these compounds with markedly increased hydrolytic stabilities are less likely to be useful in vivo as elimination through alternate pathways (excretion of the intact prodrug, oxidative metabolism, etc.) will occur before activation to the alkylating species. This hypothesis accounts for the lack of in vivo efficacy of compound 14.

A hallmark of GBM is its invasion into surrounding brain tissue at an early stage, making cure via surgical resection unachievable. As such, there is an obvious clinical need for improved compounds that can reach the entirety of the diffuse tumor in sufficient concentrations to be effective. Importantly, the data herein shows that the BBB-penetrance of imidazotetrazines can be improved through modifications at the C8 position. The dramatically enhanced brain:serum distribution of Ox-TMZ and K-TMZ, in particular, could provide substantial improvement over TMZ for treatment of CNS cancers. Both of these compounds retain the favorable features of TMZ (timely prodrug activation, stability to liver microsomes) while also accumulating higher drug concentration in the brain and reduced concentration in the blood. It was hypothesized that partitioning the imidazotetrazine more to the site of the tumor and less to the compartment responsible for adverse effects would expand the therapeutic window by enhancing anticancer activity while simultaneously reducing systemic toxicity. Myelotoxicity occurs in ~20% of TMZ-treated patients, is the major dose-limiting toxicity,[48] and is exacerbated in elderly and female GBM patients.[49,50] Ox-TMZ and K-TMZ demonstrated significantly less in vivo toxicity to WBCs compared to TMZ, likely a direct result of the increased partitioning to the CNS. Imidazotetrazines such as these with lower toxicity profiles could permit elevated dosing schedules and additional anticancer efficacy, and/or make this drug class accessible to more patients.

Other imidazotetrazines of various composition in the literature have failed to improve median survival head-to-head compared to TMZ in preclinical models, despite promising results in cell culture.[42,51,52] Only one derivative has outperformed TMZ in an intracranial murine model of GBM, bestowing a modest 10% increase in median survival.[53] Clearly, the interplay between retaining the favorable properties that have kept TMZ as frontline treatment for GBM and modulating its structure is not trivial. The data reported herein now suggest that imidazotetrazines may be substantially modified without losing these advantages, and indeed such new compounds can have dramatically enhanced in vivo efficacy. TMZ remains the gold-standard for treating the most aggressive brain tumors, shows promise against brain metastases from other cancers,[54] and its predictable activity (based on clinical biomarkers) has recently led to advocation for an expanded use of TMZ in the management of diverse cancer types.[55] As such, the novel imidazotetrazines reported here could hold considerable promise for treatment of GBM and other cancers.

TABLE 2d 7-day IC50 values (μM) for TMZ and lead C8-substituted imidazotetrazines in the Br23c GBM oncosphere cell line. Cell viability was assessed using the Alamar Blue assay. Error is SEM, n ≥0 3.

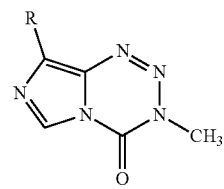

| Compound | R | MGMT – Br23C |
| --- | --- | --- |
| TMZ | CONH$_2$ | 5.2 ± 0.2 |
| 4 (Me-TMZ) | CONHMe | 6 ± 1 |
| 5 (DiMe-TMZ) | CONMe$_2$ | 6 ± 1 |
| 17 (K-TMZ) | COMe | 5.2 ± 0.3 |

General Synthetic Methods.

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, 5$^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Pharmaceutical Formulations.

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a vertebrate or mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard- or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective antitumor agents and have higher potency and/or reduced toxicity as compared to TMZ. Preferably, compounds of the invention are more potent and less toxic than TMZ, and/or avoid a potential site of catabolic metabolism encountered with TMZ, i.e., have a different metabolic profile than TMZ.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell-kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Experimental Information for Biological Data

Cell Culture and Reagents. All cell lines were grown in a 37° C., 5% $CO_2$, humidified environment, in media containing 1% penicillin/streptomycin. Cell culture conditions are as follows: traditional cell lines U87 and T98G were grown in EMEM with 10% FBS. Traditional cell lines D54 and U118MG were grown in DMEM with 10% FBS. HGCC patient-derived cell line U3054MG[1] was cultured under serum-free stem cell conditions (1:1 neurobasal:DMEM/F12 media supplemented with B27, N2, hEGF, and hFGF). GBM oncosphere cell line Br23c[2] was cultured with the NeuroCult NS-A proliferation kit (Stem Cell Technologies) supplemented with 0.0002% heparin, hEGF, and hFGF. Temozolomide (TMZ) was purchased from AK Scientific. TMZ analogs were synthesized as described below. Compounds were dissolved in DMSO (1% final concentration, Fisher Chemical) for cell culture studies.

Cell Viability Assays. Cells were harvested, seeded in a 96-well plate and allowed to adhere. After three hours, compound was added to each well in DMSO (1% final concentration). Cells were incubated for seven days before viability was assessed by the Alamar Blue Assay. Raptinal (20 µM) was used as a dead control.

Mouse Liver Microsome Stability Assay. A mixture of PBS (pH 7.4), NADPH regenerating system solution A (Corning Life Sciences), and NADPH regenerating system solution B (Corning Life Sciences) was incubated at 37° C. in a shaking incubator for 5 min. Next, compound was added in DMSO (final concentration 50 µM, 0.5% DMSO) before ice-cold mouse liver microsomes (Thermo Fisher, male CD-1 mice, pooled) were added (final protein concentration of 1 mg/mL). An aliquot was immediately removed, quenched with an equal volume of 100 µM internal standard and 0.5% hydrochloric acid in ice-cold acetonitrile, and centrifuged at 13,000 rcf for 3 min. The supernatant was diluted 1:5 in $ddH_2O$ and analyzed by LC-MS. The reactions were incubated at 37° C. in a shaking incubator for 2 h. A second aliquot was removed, quenched and diluted as before and analyzed by LC-MS. The ratio of the areas of analyte: internal standard at 2 hours was compared to the ratio at $t_0$ to determine the percentage of compound remaining. Analysis was performed on an Agilent 6230 LC/MS TOF system with a 1.8 µm, 2.1×50 mm Agilent ZORBAX Eclipse Plus C18 column. Internal standard=N3-propyl TMZ.

$O^6$-Methyldeoxyguanosine Quantitation. U87 cells were plated at $1×10^6$ c/w in a 6-well plate before they were treated with compound at the indicated concentration (1% final concentration DMSO). After 8 h incubation, the cells were harvested and pelleted. Genomic DNA was extracted using the DNeasy Blood & Tissue Kit (Qiagen, ID: 69504). DNA was then precipitated using the following procedure: 1/10 v/v 3M sodium acetate (pH 5.2) and 2.5× v/v ethanol was added to each sample which was then kept at −80° C. for 1 h. The mixture was centrifuged at max at 4° C. for 30 min and decanted to afford a pellet of DNA, which was re-suspended in $ddH_2O$ containing 10 mM tris base (pH 7.5) and 1 mM EDTA. The concentration of DNA in each sample was quantified measuring absorbance on a NanoDrop 2000 UV-Vis Spectrophotometer (Thermo Fisher). DNA (10 µg) from each sample was added to DNA hydrolysis buffer[3] and incubated at 37° C. for 6 h. Hydrolyzed samples were then submitted for LC-MS/MS quantitation. Samples were analyzed with a 5500 QTRAP LC/MS/MS system (AB Sciex) with a 1200 series HPLC system (Agilent).

in vivo Blood-Brain Barrier Permeability. All experimental procedures were reviewed and approved by the University of Illinois Institutional Animal Care and Use Committee. CD-1 IGS mice were administered compound in 1% DMSO (FIG. 2a) or 10% DMSO (FIG. 2b-d) in PBS at 25 mg/kg via lateral tail vein injection. Five minutes post injection, mice were sacrificed, and blood was collected by lacerating the right auricle with iris scissors. An 18-gauge angiocatheter was inserted through the left ventricle, and all residual circulatory volume was removed by perfusing 0.9% saline solution via an analog peristaltic pump. Blood samples were immediately centrifuged at 13,000 rcf for five minutes and the supernatant collected and acidified with 8.5% aqueous $H_3PO_4$. Brains were harvested from the cranial vault, acidified with 0.3% aqueous $H_3PO_4$ and flash frozen. Homogenized brain samples were centrifuged twice at 13,000 rcf for ten minutes and supernatant and tissue debris were separated. The resultant supernatant was analyzed, along with plasma, by LC-MS/MS to determine compound concentrations. In order to calculate absolute brain:serum ratios (ng $drug_{brain}$:ng $drug_{serum}$), a mouse blood volume of 58.5 mL/kg was assumed for each mouse.

in vivo Efficacy Models. Human GBM Br23c stem-like neurosphere cells were intracranially implanted in female athymic nude mice (150,000 cells/mouse). Beginning day 5 after implantation of the tumor cells, drugs were formulated in 10% PEG 400 in saline and 15 mg/kg TMZ (or equimolar dose of C8 analog) was administered via oral gavage once-per-day for 7 weeks (FIG. 5a) or once-per-day for 5 total treatments (FIG. 5b). TMZ and C8 analogs were dissolved fresh for each use. Mice were observed daily for any signs of deterioration, neurotoxicity, or movement disorders. They were inspected for signs of pain and distress, as in accordance with the Johns Hopkins Animal Care and Use Guidelines. If the symptoms persisted and resulted in debilitation, the animals were euthanized according to protocol.

Assessment of Hematological Toxicity. Male CD-1 IGS mice (n=4 mice/group) were administered a single dose of 125 mg/kg compound intravenously. Imidazotetrazines were formulated with SBEβCD in sterile water immediately prior to injection. Seven days post-treatment, mice were humanely sacrificed and whole blood was collected for assessment of total white blood cells, lymphocytes, neutrophils, platelets, and red blood cells.

Example 2. Synthetic Methods

Materials and Methods. Chemical reagents were purchased from commercial sources and used without further purification. Flash chromatography was performed using silica gel (230-400 mesh). Anhydrous solvents were dried after being passed through columns packed with activated alumina under positive pressure of nitrogen. Unless otherwise noted, all reactions were carried out in oven-dried glassware with magnetic stirring under nitrogen atmosphere. $^1$H and $^{13}$C NMR spectra were recorded on Bruker 500 (500 MHz, $^1$H; 125 MHz, $^{13}$C) or Varian Unity Inova 500 (500 MHz, $^1$H) MHz spectrometers. Spectra are referenced to residual chloroform (δ=7.26 ppm, $^1$H; 77.16 ppm, $^{13}$C) or dimethyl sulfoxide (δ=2.50 ppm, $^1$H; 39.52 ppm, $^{13}$C). Multiplicities are indicated by s (singlet), d (doublet), t (triplet), q (quartet), m (multiplet), and br (broad). Coupling constants J are reported in Hertz (Hz). High resolution mass spectrometry (HRMS) was performed on a Waters Q-Tof Ultima or Waters Synapt G2-Si instrument with electrospray ionization (ESI) or electron impact ionization (EI).

Preparation and Characterization of C8 Analogs. Experimental information for compounds 3,[4] 9,[5] 11,[6] 15,[7] 16,[8] 29,[9] 31,[10] and 33[6] has been previously reported.

General Scheme for Preparation of Amide, Ester, and Thioester Derivatives 4-10:

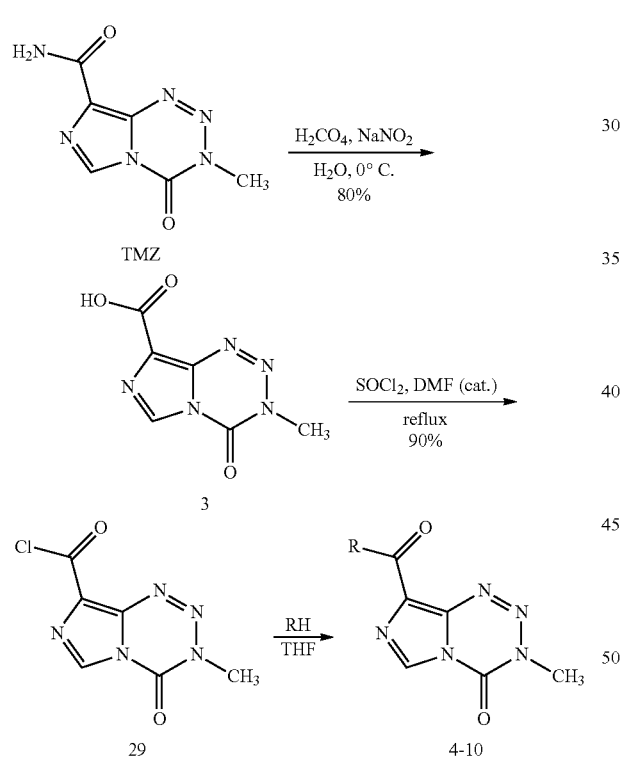

General procedure for preparation of 4-10. In an oven-dried 25 mL round bottom flask, acyl chloride 29 (148.6 mg, 0.70 mmol, 1 eq.) was dissolved in anhydrous THF (2.8 mL, 0.25 M). Methylamine (33% w/w in ethanol, 0.09 mL, 0.73 mL, 1.05 eq.) was then added and the reaction was stirred for 3 h at room temperature. When complete, the reaction was stopped and the solvent was evaporated. The crude solid was purified by flash silica gel chromatography (100% ethyl acetate) to yield 98.3 mg (68%) of pure 4 as a white solid.

Experimental data for compounds 3, 9, and 29 has been published.[4,5,9]

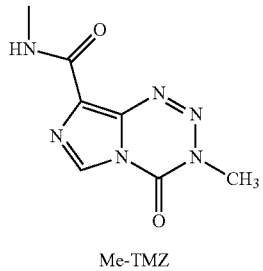

Me-TMZ (4)

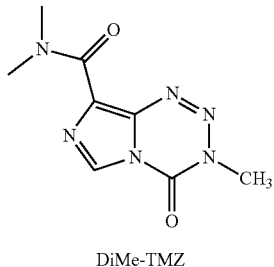

DiMe-TMZ (5)

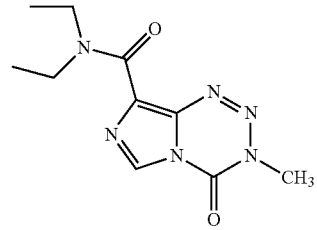

6

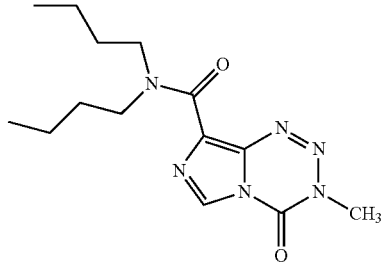

7

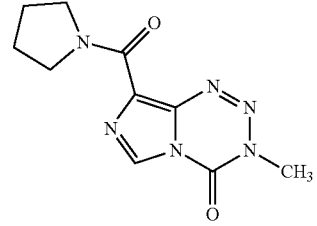

8

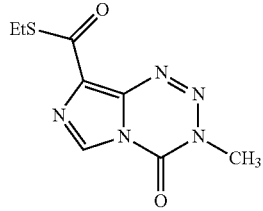

10

N,3-dimethyl-4-oxo-3,4-dihydroimidazo[5,1-d][1,2,3,5]tetrazine-8-carboxamide (4, Me-TMZ): $^1$H NMR (500 MHz, d-DMSO) δ 8.84 (s, 1H), 8.45 (d, J=4.9 Hz, 1H), 3.86 (s, 3H), 2.81 (d, J=4.8 Hz, 3H). $^{13}$C (125 MHz, d-DMSO) δ

160.13, 139.23, 134.27, 130.54, 128.44, 36.14, 25.80. HRMS (ESI) calc. for $C_7H_8N_6O_2Na$, $[M+Na]^+$: 231.0606. Found: 231.0608.

N,N,3-trimethyl-4-oxo-3,4-dihydroimidazo[5,1-d][1,2,3,5]tetrazine-8-carboxamide (5, DiMe-TMZ): 76% yield as a white solid. $^1H$ NMR (500 MHz, d-DMSO) δ 8.81 (s, 1H), 3.85 (s, 3H), 3.06 (s, 6H). $^{13}C$ NMR (125 MHz, d-DMSO) δ 161.76, 139.22, 133.57, 132.05, 128.59, 38.12, 36.05, 34.84. HRMS (ESI) calc. for $C_8H_{11}N_6O_2$, $[M+H]^+$: 223.0938. Found: 223.0943.

N,N-diethyl-3-methyl-4-oxo-3,4-dihydroimidazo[5,1-d][1,2,3,5]tetrazine-8-carboxamide (6): 91% as a white solid. $^1H$ NMR (500 MHz, d-DMSO) δ 8.81 (s, 1H), 3.84 (s, 3H), 3.49 (q, J=7.1 Hz, 2H), 3.38 (q, J=7.0 Hz, 2H), 1.18 (t, J=7.1 Hz, 3H), 1.11 (t, J=7.0 Hz, 3H). $^{13}C$ NMR (125 MHz, d-DMSO) δ 161.35, 139.24, 133.54, 132.72, 128.45, 42.53, 36.01, 14.43, 12.80. HRMS (ESI) calc. for $C_{10}H_{15}N_6O_2$, $[M+H]^+$: 251.1256. Found: 251.1250.

N,N-dibutyl-3-methyl-4-oxo-3,4-dihydroimidazo[5,1-d][1,2,3,5]tetrazine-8-carboxamide (7): 85% yield as a white solid. $^1H$ NMR (500 MHz, d-DMSO) δ 8.80 (s, 1H), 3.84 (s, 3H), 3.45 (m, 2H), 3.34 (m, 2H), 1.59 (m, 2H), 1.49 (m, 2H), 1.35 (h, J=7.4 Hz, 2H), 1.11 (h, J=7.4 Hz, 2H), 0.94 (t, J=7.4 Hz, 3H), 0.76 (t, J=7.4 Hz, 3H). $^{13}C$ NMR (125 MHz, d-DMSO) δ 161.74, 139.23, 133.35, 132.80, 128.42, 47.66, 44.41, 35.99, 30.54, 29.20, 19.65, 19.17, 13.79, 13.55. HRMS (ESI) calc. for $C_{14}H_{23}N_6O_2$, $[M+H]^+$: 307.1882. Found: 307.1881.

3-methyl-8-(pyrrolidine-1-carbonyl)imidazo[5,1-d][1,2,3,5]tetrazin-4(3H)-one (8): 55% yield as pale-yellow solid. $^1H$ NMR (500 MHz, d-DMSO) δ 8.81 (s, 1H), 3.85 (s, 3H), 3.63 (m, 2H), 3.53 (m, 2H), 1.88 (m, 4H). $^{13}C$ NMR (125 MHz, d-DMSO) δ 159.73, 139.21, 134.07, 132.54, 128.33, 48.05, 46.09, 36.05, 25.80, 23.63. HRMS (ESI) calc. for $C_{10}H_{13}N_6O_2$, $[M+H]^+$: 249.1100. Found: 249.1105.

S-ethyl 3-methyl-4-oxo-3,4-dihydroimidazo[5,1-d][1,2,3,5]tetrazine-8-carbothioate (10): 92% as a white solid. $^1H$ NMR (500 MHz, d-DMSO) δ 8.86 (s, 1H), 3.89 (s, 3H), 3.02 (q, J=7.4 Hz, 2H), 1.28 (t, J=7.4 Hz, 3H). $^{13}C$ NMR (125 MHz, d-DMSO) δ 184.57, 138.95, 133.80, 131.55, 129.19, 36.50, 22.15, 14.70. HRMS (ESI) calc. for $C_8H_{10}N_5O_2S$, $[M+H]^+$: 240.0555. Found: 240.0551.

3,8-dimethylimidazo[5,1-d][1,2,3,5]tetrazin-4(3H)-one (14)

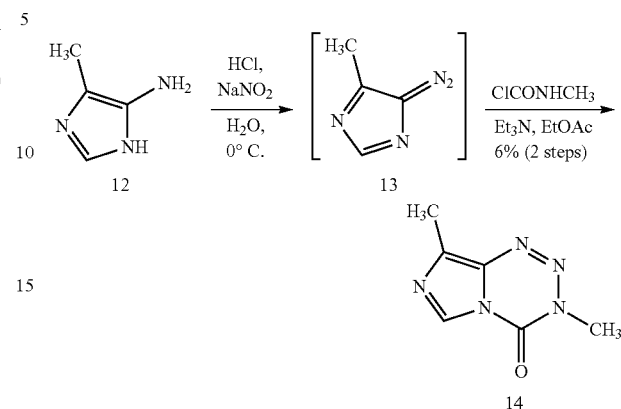

Procedure. To a 15 mL round bottom flask, 4-methyl-1H-imidazol-5-amine dihydrochloride 12 (44.2 mg, 0.3 mmol, 1 eq.) was added and dissolved in 1M HCl (0.4 mL, 0.65 M) before sodium nitrite (26.2 mg, 0.4 mmol, 1.5 eq.) in water (0.4 mL, 0.65 M) was added at 0° C. in the dark. The solution was stirred 30 minutes then concentrated and azeotroped twice with toluene to afford crude diazo 13. To the crude diazo suspended in ethyl acetate (1.3 mL, 0.2 M), anhydrous triethylamine (0.08 mL, 0.6 mmol, 2.2 eq.) and methylcarbamic chloride (79 mg, 0.8 mmol, 3.2 eq.) were added in the dark. The reaction was stirred overnight before being purified via flash silica gel chromatography (4:1 hexanes ethyl acetate) to afford 2.4 mg (6%) 14 as a pale yellow solid. Note: To minimize decomposition of the crude diazo species, concentration was done (without heating) in the dark as quickly as possible. $^1H$ NMR (500 MHz, d-CHCl$_3$) δ 8.35 (s, 1H), 3.94 (s, 3H), 2.66 (s, 3H). $^{13}C$ NMR (125 MHz, d-CHCl$_3$) δ 139.71, 139.64, 132.51, 127.94, 35.76, 12.53. HRMS (EI) calc. for $CH_7N_5O$, $[M]^+$: 165.0651. Found: 165.0654.

8-acetyl-3-methylimidazo[5,1-d][1,2,3,5]tetrazin-4(3H)-one (17, K-TMZ)

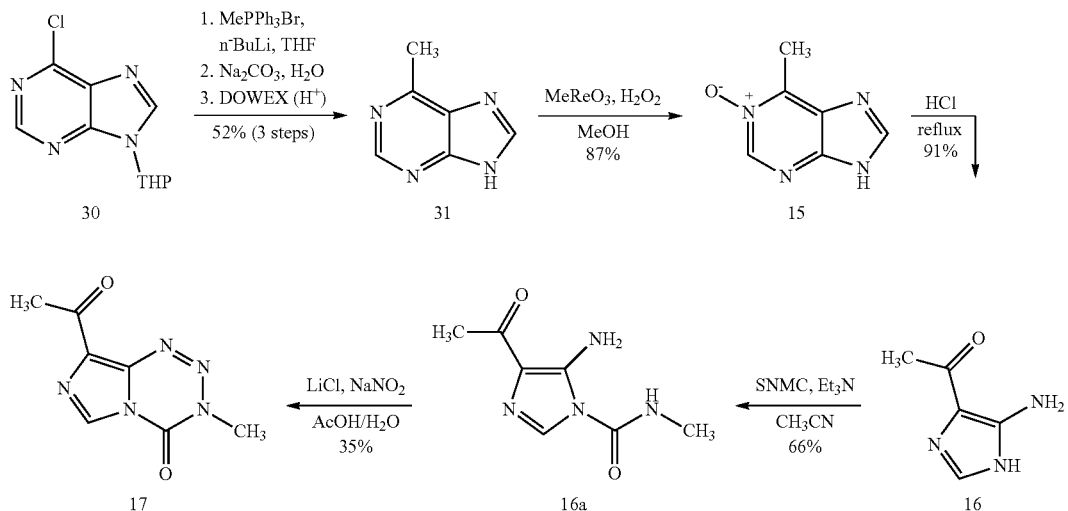

Procedure. To an oven-dried 25 mL round bottom flask, 16 (186 mg, 0.89 mmol, 1 eq.) and N-succinimidyl N-methylcarbamate (321 mg, 1.86 mmol, 2.1 eq.) were added and suspended in anhydrous acetonitrile (1.5 mL, 0.6 M). Next, under nitrogen, dry triethylamine (0.34 mL, 2.4 mmol, 2.7 eq.) was added slowly and the solution was stirred overnight at room temperature. Upon completion, the mixture was concentrated and purified by silica gel flash chromatography (100% dichloromethane to 4:1 dichloromethane:methanol) to afford 106 mg (66%) of intermediate 16a as a gold solid. $^1$H NMR (500 MHz, d-DMSO) δ 8.17 (br s, 1H), 7.97 (s, 1H), 7.56 (s, 2H), 3.36 (d, J=4.5 Hz, 3H), 2.73 (s, 3H).

In a 15 mL round bottom flask, LiCl (802 mg, 19 mmol, 36 eq.) was dissolved in distilled water (1.3 mL, 0.4 M) and AcOH (0.10 mL, 5.3 M) and stirred for thirty minutes until the exotherm dissipated. Intermediate 16a (96.3 mg, 0.53 mmol, 1 eq.) was added in one portion and stirred for thirty minutes. The suspension was then cooled to 0° C. in an ice bath before a solution of NaNO$_2$ (57 mg, 0.8 mmol, 1.5 eq.) in a minimal amount of distilled water was added dropwise. The resultant mixture was stirred at 0° C. for 30 minutes, then warmed to room temperature and stirred an additional 5 hours. Upon completion, the reaction mixture was diluted with CH$_2$Cl$_2$ and the organic layer was separated. The aqueous layer was extracted with dichloromethane (×6) and the combined organic layers were dried over sodium sulfate and concentrated to yield crude solid which was purified by flash silica chromatography (1:1 ethyl acetate:hexanes) to afford 36 mg (35%) of 17 as a white solid. $^1$H NMR (500 MHz, d-DMSO) δ 8.86 (s, 1H), 3.90 (s, 3H), 2.68 (s, 3H). $^{13}$C NMR (125 MHz, d-DMSO) δ 191.47, 139.01, 135.56, 133.35, 129.11, 36.43, 28.31. HRMS (ESI) calc. for C$_7$H$_8$N$_5$O$_2$, [M+H]$^+$: 194.0678. Found: 194.0683.

Experimental data for intermediates 31, 15, and 16 has been published.[7,8,10]

8-bromo-3-methylimidazo[5,1-d][1,2,3,5]tetrazin-4(3H)-one (18)

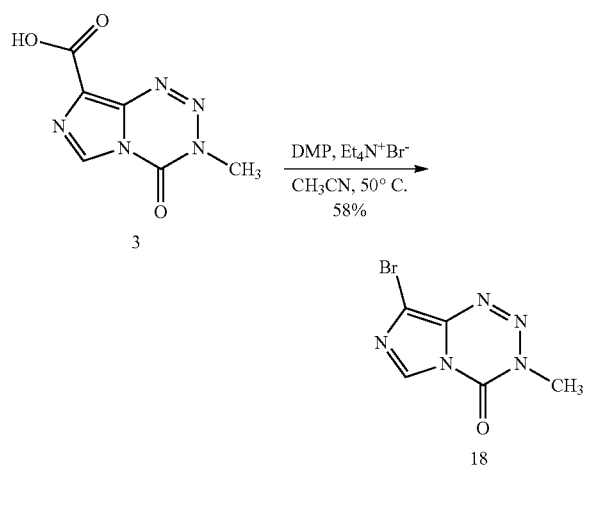

Procedure. To a stirred suspension of Dess-Martin periodinane (477 mg, 1.12 mmol, 2.2 eq) in anhydrous CH$_3$CN (2.6 mL, 0.2 M), tetraethylammonium bromide (240 mg, 1.12 mmol, 2.2 eq) was added. Reaction was stirred 5 min at room temperature before 3 (100 mg, 0.51 mmol, 1 eq) was added. The resultant reaction mixture was heated at 50° C. for 2 h. Upon completion, the solvent was concentrated under reduced pressure to give the crude product that was purified by flash silica gel chromatography (9:1 hexanes:ethyl acetate) to afford 73 mg (58%) of 18 as a white solid. $^1$H NMR (500 MHz, CDCl$_3$) δ 8.37 (s, 1H), 3.98 (s, 3H). $^{13}$C NMR (125 MHz, CDCl$_3$) δ 138.74, 133.32, 128.56, 117.16, 36.43. HRMS (ESI) calc. for C$_5$H$_5$N$_5$OBr, [M+H]$^+$: 229.9677. Found: 229.9684.

8-chloro-3-methylimidazo[5,1-d][1,2,3,5]tetrazin-4(3H)-one (19)

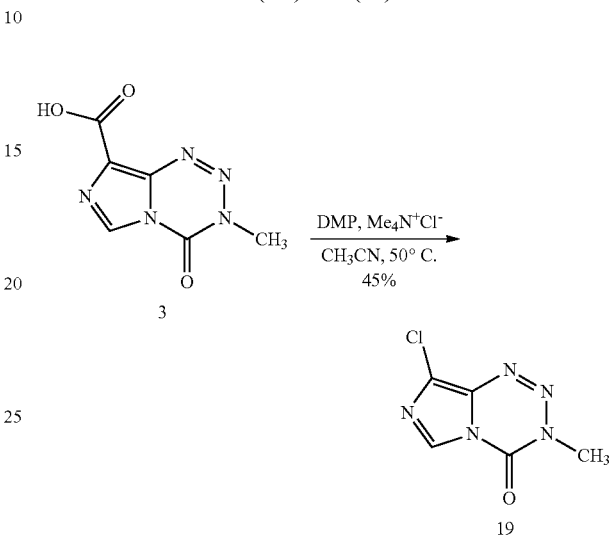

Procedure. To a stirred suspension of Dess-Martin periodinane (477 mg, 1.12 mmol, 2.2 eq.) in anhydrous CH$_3$CN (2.6 mL, 0.2 M), tetramethylammonium chloride (123 mg, 1.12 mmol, 2.2 eq.) was added. The reaction was stirred 5 min at room temperature before 3 (100 mg, 0.51 mmol, 1 eq.) was added. The resultant reaction mixture was heated at 50° C. for 2 hours. Upon completion, the solvent was concentrated under reduced pressure to give the crude product that was purified by flash silica chromatography (9:1 hexanes:ethyl acetate) to afford 43 mg (45%) of 19 as a white solid. $^1$H NMR (500 MHz, CDCl$_3$) δ 8.33 (s, 1H), 3.98 (s, 3H). $^{13}$C NMR (125 MHz, CDCl$_3$) δ 138.74, 130.84, 129.81, 127.25, 36.37. HRMS (ESI) calc. for C$_5$H$_5$N$_5$OCl, [M+H]$^+$: 186.0183. Found: 186.0186.

General Scheme for Preparation of Aryl Derivatives 23-26:

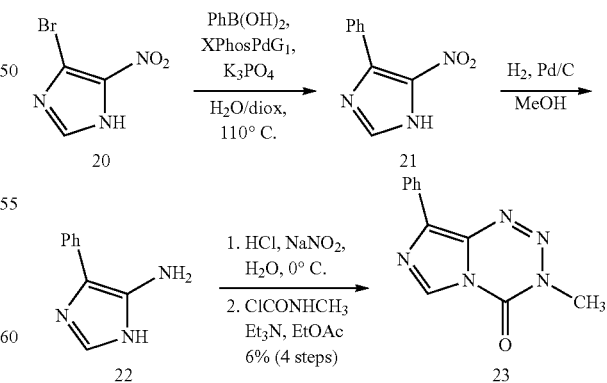

General Procedure for Preparation of 23-26. (a) Suzuki Coupling. A mixture of 4-bromo-5-nitro-1H-imidazole 20 (400 mg, 2.08 mmol, 1 eq.), phenyl boronic acid (507 mg, 4.17 mmol, 2 eq.), XPhosPdG$_1$ (164 mg, 0.2 mmol, 0.1 eq.)

and $K_3PO_4$ (1.32 g, 6.24 mmol, 3 eq.) under nitrogen was suspended in degassed 1:1 $H_2O$:dioxane (16 mL, 0.13 M). The resulting mixture was stirred at 110° C. for 16 h. The reaction was cooled to room temperature and $H_2O$ was added. The aqueous layer was extracted ×3 with ethyl acetate and the combined organic layers were dried over $Na_2SO_4$ and concentrated. The residue obtained was purified by flash silica gel chromatography (100% ethyl acetate) to afford crude product 21 that was used for next step without further purification.

(b) Nitro Reduction. Crude 21 was dissolved in dry MeOH (10 mL, 0.2 M) containing 10% Pd/C before $H_2$ (1 atm) was introduced. The reaction was stirred for 16 h at room temperature before the catalyst was filtered over Celite. The filtrate was concentrated under reduced pressure and purified by flash silica gel chromatography (95:5 DCM: MeOH) providing compound 22 that was used for next step without further purification.

(c) Cyclization. To a suspension of intermediate 22 in 1 M HCl (2.9 mL, 0.7 M) at 0° C. was added a pre-formed solution of $NaNO_2$ (186 mg, 2.7 mmol, 1.3 eq.) in $H_2O$ (2.9 mL, 0.9 M) dropwise. The resultant mixture was stirred at 0° C. in the dark for 30 min. Upon completion, the solvent was evaporated, and the crude diazo compound was dissolved in ethyl acetate (9.6 mL, 0.2 M) before triethylamine (544 µL, 4.6 mmol, 2 eq.) and methylcarbamic chloride (1010 mg, 10.8 mmol, 5.2 eq.) were added. The reaction mixture was stirred at room temperature for 16 h protected from light. Upon reaction completion, the solvent was concentrated under reduced pressure and the residue was purified by flash silica gel chromatography (9:1 hexanes:ethyl acetate) to afford 28 mg (6%) of pure 23 as a white solid.

3-methyl-8-phenylimidazo[5,1-d][1,2,3,5]tetrazin-4(3H)-one (23)

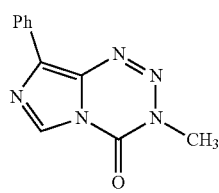

23

Product was obtained using the general procedure. White solid, 6% yield (4 steps). $^1$H NMR (500 MHz, d-DMSO) δ 8.84 (s, 1H), 8.31-8.29 (m, 2H), 7.57-7.53 (m, 2H), 7.44 (tt, J=7.4, 1.3 Hz, 1H), 3.85 (s, 3H). $^{13}$C NMR (125 MHz, $CDCl_3$) δ 140.02, 137.02, 132.30, 131.88, 129.86, 129.48, 129.43, 127.07, 36.29. HRMS (ESI) calc. for $C_{11}H_{10}N_5O$, $[M+H]^+$: 228.0885. Found: 228.0878.

8-(4-fluorophenyl)-3-methylimidazo[5,1-d][1,2,3,5]tetrazin-4(3H)-one (24)

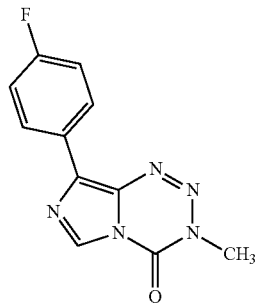

24

Product was obtain using the general procedure. Yellow solid, 3% yield (4 steps). $^1$H NMR (500 MHz, $CDCl_3$) δ 8.46 (s, 1H), 8.44-8.40 (m, 2H), 7.24-7.19 (m, 2H), 4.01 (s, 3H). $^{13}$C NMR (125 MHz, $CDCl_3$) δ 164.57, 162.58, 139.20 (d, J=86.4 Hz, 1C), 131.00, 129.43 (d, J=8.3 Hz, 1C), 128.56, 127.26 (d, J=3.3 Hz, 1C), 116.00 (d, J=21.6 Hz, 1C), 35.97. HRMS (ESI) calc. for $C_{11}H_9FN_5O$, $[M+H]^+$: 246.0791. Found: 246.0788.

3-methyl-8-(4-(trifluoromethyl)phenyl)imidazo[5,1-d][1,2,3,5]tetrazin-4(3H)-one (25)

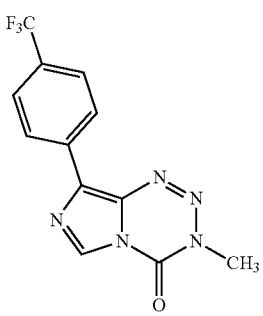

25

Product was obtained using the general procedure. Yellow solid, 5% yield (4 steps). $^1$H NMR (500 MHz, $CDCl_3$) δ 8.52 (d, J=8.2 Hz, 2H), 8.48 (s, 1H), 7.75 (d, J=8.2 Hz, 2H), 4.02 (s, 3H). $^{13}$C NMR (125 MHz, $CDCl_3$) δ 139.34, 137.89, 134.30, 131.91, 131.03 (q, J=32.3 Hz, 1C), 128.77, 127.61, 125.80 (q, J=3.8 Hz, 1C), 122.96, 36.15. HRMS (ESI) calc. for $C_{12}H_9N_5OF_3$, $[M+H]^+$: 296.0759. Found: 296.0754.

8-(4-chlorophenyl)-3-methylimidazo[5,1-d][1,2,3,5]tetrazin-4(3H)-one (26)

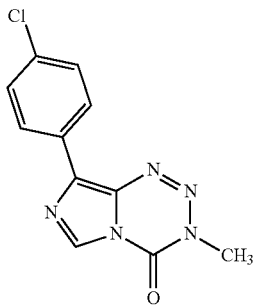

26

Product was obtained using the general procedure. Yellow solid, 1.2% yield (4 steps). $^1$H NMR (500 MHz, d-DMSO) δ 8.86 (s, 1H), 8.30 (dt, J=9.25, 2.5 Hz, 2H), 7.62 (dt, J=9.25, 2.5 Hz, 2H), 3.86 (s, 3H). $^{13}$C NMR (125 MHz, d-DMSO) δ 139.92, 135.67, 133.97, 132.45, 130.75, 130.00, 129.63, 128.62, 36.37. HRMS (ESI) calc. for $C_{11}H_9N_5OCl$, [M+H]$^+$: 262.0496. Found: 262.0489.

3-methyl-4-oxo-N-(2-oxopropyl)-3,4-dihydroimidazo[5,1-d][1,2,3,5]tetrazine-8-carboxamide (32)

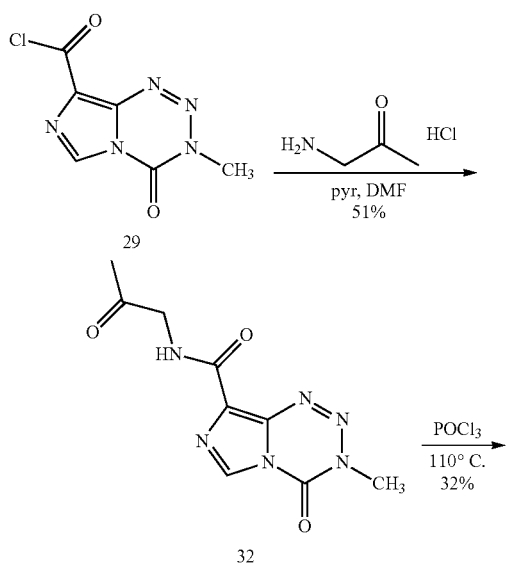

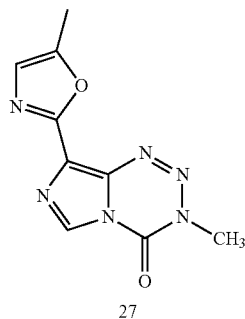

27

Procedure. To 29 (447 mg, 2.09 mmol, 1 eq.) and 2-aminoacetophenone hydrochloride (229 mg, 2.09 mmol, 1 eq.) was added DMF (4.4 mL, 0.47 M) and pyridine (0.9 mL). The reaction mixture was stirred for 16 h at room temperature. Water was added and the aqueous layer was extracted x5 with ethyl acetate. The combined organic layers were dried over $Na_2SO_4$ and concentrated. The residue obtained was purified by flash silica gel chromatography (100% ethyl acetate) to afford 266 mg (51%) of 32 as an orange solid. $^1$H NMR (500 MHz, d-DMSO) δ 8.87 (s, 1H), 8.59 (t, J=5.7 Hz, 1H), 4.17 (d, J=5.7 Hz, 2H), 3.88 (s, 3H), 2.15 (s, 3H). $^{13}$C NMR (125 MHz, d-DMSO) δ 204.55, 160.15, 139.65, 135.10, 130.18, 129.09, 49.57, 36.67, 27.52. LC-MS (ESI) calc. for $C_9H_{11}N_6O_3$ [M+H]$^+$: 251.0893, found: 251.09.

3-methyl-8-(5-methyloxazol-2-yl)imidazo[5,1-d][1,2,3,5]tetrazin-4(3H)-one (27, Ox-TMZ)

Procedure: Intermediate 32 (266 mg, 1.06 mmol, 1 eq.) was added to phosphoryl chloride (6.5 mL, 0.16 M) and the stirred mixture was heated at 110° C. for 3 h. Upon completion, ice water was added, and the aqueous layer was extracted x4 with ethyl acetate. The combined organic layers were dried over $Na_2SO_4$ and concentrated. The residue obtained was purified by flash silica gel chromatography (100% ethyl acetate) to afford 80 mg (32%) of the product 27 as a yellow solid. $^1$H NMR (500 MHz, d-DMSO) δ 8.89 (s, 1H), 7.13 (br d, J=1.2 Hz, 1H), 3.87 (s, 3H), 2.44 (d, J=1.2 Hz, 3H). $^{13}$C NMR (125 MHz, d-DMSO) δ 154.15, 150.47, 139.64, 133.64, 130.43, 126.15, 125.36, 36.56, 11.17. HRMS (ESI) calc. for $C_9H_9N_6O_2$, [M+H]$^+$: 233.0782. Found: 233.0787.

The route to 4-substituted oxazol-2-yls at the C8 position of imidazotetrazines is known,[11] however, the synthesis of compound 27 via intermediate 32 had never been reported.

3-methyl-4-oxo-3,4-dihydroimidazo[5,1-d][1,2,3,5]tetrazine-8-carbothioamide (28)

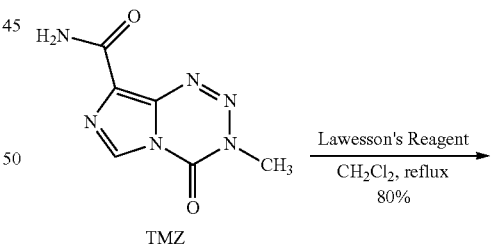

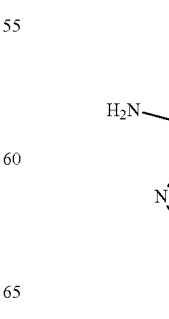

33

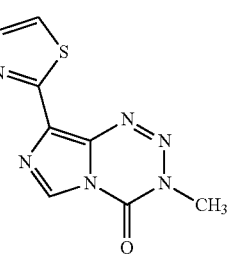

28

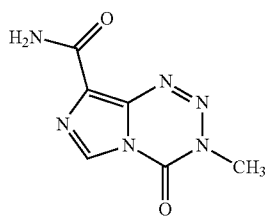

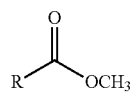

Procedure. To a solution of 33 (550 mg, 2.6 mmol, 1 eq.) in acetonitrile (40 mL, 0.07 M) was added α-Bromo acetone (220 µL, 2.6 mmol, 1 eq.) and the solution was stirred at room temperature for 18 h. Upon completion, the reaction was stopped, and the precipitate was filtered and purified by flash silica gel chromatography (4:6 hexanes:ethyl acetate) to afford 167 mg (26%) of the desired product 28 as a yellow solid. $^1$H NMR (500 MHz, d-DMSO) δ 8.87 (s, 1H), 7.46 (d, J=0.9 Hz, 1H), 3.86 (s, 3H), 2.48 (d, J=0.9 Hz, 3H). $^{13}$C NMR (125 MHz, d-DMSO) b 158.63, 154.58, 139.75, 131.84, 131.80, 130.24, 116.56, 36.52, 17.45. HRMS (ESI) calc. for $C_9H_9N_6OS$, [M+H]$^+$: 249.0559. Found: 249.0559.

The route to 4-substituted thiazol-2-yls at the C8 position of imidazotetrazines is known[11], however, the synthesis of compound 28 had never been reported. Experimental data for intermediate 33 has been published.[6]

Example 3. Synthesis of Arene, Propargyl, and Diazoalkane Compounds

Arene and propargyl substituted imidazotetrazines can be prepared as follows.

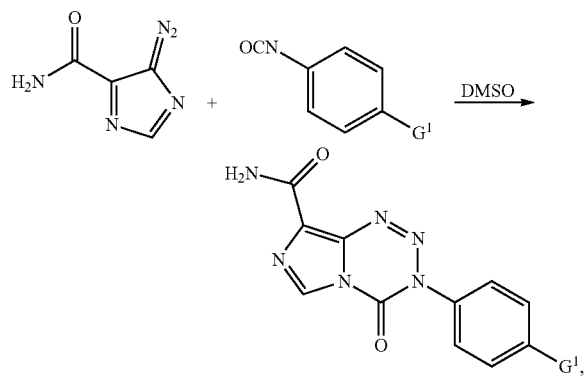

wherein G$^1$ is OCH$_3$, OCH$_2$CH$_3$, OPh, N(CH$_3$)$_2$, propargyl, or a substituent as defined herein.

TMZ is a non-explosive, weighable surrogate for diazomethane. TMZ and other imidazotetrazines can be used as synthetic diazoalkane precursors as illustrated below.

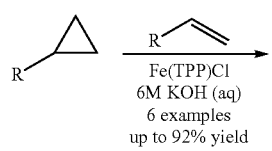

Example 4. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/tablet |
|---|---|
| 'Compound X' (free acid form) | 1.0 |
| Dibasic sodium phosphate | 12.0 |
| Monobasic sodium phosphate | 0.7 |

| (iv) Injection 1 (1 mg/mL) | mg/tablet |
|---|---|
| Sodium chloride | 4.5 |
| 1.0N Sodium hydroxide solution (pH) adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

CITATIONS (1) Stupp, R.; Mason, W.; van den Bent, M. J.; Weller, M.; Fisher, B. M.; Taphoorn, M. J. B.; Belanger, K.; Brandes, A. A.; Marosi, C.; Bogdahn, U.; Curschmann, J.; Janzer, R. C.; Ludwin, S. K.; Gorlia, T.; Allgeier, A.; Lacombe, D.; Cairncross, J. G.; Eisenhauer, E.; Mirimanoff, R. O. (2005) Radiotherapy plus Concomitant and Adjuvant Temozolomide for Glioblastoma. N. Engl. J. Med. 352, 987-996.

(2) Denny, B. J.; Wheelhouse, R. T.; Stevens, M. F.; Tsang, L. L.; Slack, J. a. (1994) NMR and Molecular Modeling Investigation of the Mechanism of Activation of the Antitumor Drug Temozolomide and Its Interaction with DNA. Biochemistry 33, 9045-9051.

(3) Karran, P.; Macpherson, P.; Ceccotti, S.; Dogliotti, E.; Griffin, S.; Bignami, M. (1993) 06-Methylguanine Residues Elicit DNA Repair Synthesis by Human Cell Extracts. J. Biol. Chem. 268, 15878-15886.

(4) Ceccotti, S.; Aquilina, G.; Macpherson, P.; Yamada, M.; Karran, P.; Bignami, M. (1996) Processing of 06-Methylguanine by Mismatch Correction in Human Cell Extracts. Curr. Biol. 6, 1528-1531.

(5) Margison, G. P.; Santibanez Koref, M. F.; Povey, A. C. (2002) Mechanisms of Carcinogenicity/Chemotherapy by 06-Methylguanine. Mutagenesis 17, 483-487.

(6) Tisdale, M. J. (1987) Antitumour Imidazotetrazines-XV. Role of Guanine 06 Alkylation in the Mechanism of Cytotoxicity of Imidazotetrazinones. Biochem. Pharmacol. 36, 457-462.

(7) Newlands, E. S.; Blackledge, G. R.; Slack, J. A.; Rustin, G. J.; Smith, D. B.; Stuart, N. S.; Quarterman, C. P.; Hoffman, R.; Stevens, M. F.; Brampton, M. H.; Gibson, A. C. (1992) Phase I Trial of Temozolomide (CCRG 81045: M&B 39831: NSC 362856). Br. J. Cancer 65, 287-291.

(8) Ostermann, S.; Csajka, C.; Buclin, T.; Leyvraz, S.; Lejeune, F.; Decosterd, L. a; Stupp, R. (2004) Plasma and Cerebrospinal Fluid Population Pharmacokinetics of Temozolomide in Malignant Glioma Patients. Clin. Cancer Res. 10, 3728-3736.

(9) Portnow, J.; Badie, B.; Chen, M.; Liu, A.; Blanchard, S.; Synold, T. W. (2009) The Neuropharmacokinetics of Temozolomide in Patients with Resectable Brain Tumors: Potential Implications for the Current Approach to Chemoradiation. Clin. Cancer Res. 15, 7092-7098.

(10) Stupp, R.; Hegi, M. E.; Mason, W. P.; van den Bent, M. J.; Taphoorn, M. J.; Janzer, R. C.; Ludwin, S. K.; Allgeier, A.; Fisher, B.; Belanger, K.; Hau, P.; Brandes, A. A.; Gijtenbeek, J.; Marosi, C.; Vecht, C. J.; Mokhtari, K.; Wesseling, P.; Villa, S.; Eisenhauer, E.; Gorlia, T.; Weller, M.; Lacombe, D.; Cairncross, J. G.; Mirimanoff, R. O. (2009) Effects of Radiotherapy with Concomitant and Adjuvant Temozolomide versus Radiotherapy Alone on Survival in Glioblastoma in a Randomised Phase III Study: 5-Year Analysis of the EORTC-NCIC Trial. Lancet Oncol. 10, 459-466.

(11) Reifenberger, G.; Wirsching, H.-G.; Knobbe-Thomsen, C. B.; Weller, M. (2017) Advances in the Molecular Genetics of Gliomas—Implications for Classification and Therapy. Nat. Rev. Clin. Oncol. 14, 434-452.

(12) Vaupel, P.; Kallinowski, F.; Okunieff, P. (1989) Blood Flow, Oxygen and Nutrient Supply, and Metabolic Microenvironment of Human Tumors: A Review. Cancer Res. 49, 6449-6465.

(13) Rottenberg, D. A., Ginos, J. Z., Kearfott, K. J., Junck, L., and Bigner, D. D. (1984) In Vivo Measurement of Regional Brain Tissue PH Using Positron Emission Tomography. Ann. Neurol. 15, S98-S102.

(14) Arnold, James B, Kraig, Richard P, Rottenberg, D. A. (1986) In Vivo Measurement of Regional Brain and Tumor pH Using [14 C]Dimethyloxazolidinedione and Quantitative Autoradiography. II: Characterization of the Extracellular Fluid Compartment Using PH-Sensitive Microelectrodes and [14 C]Sucrose. J. Cereb. Blood Flow Metab. 6, 435-440.

(15) McLean, L. A.; Roscoe, J.; Jorgensen, N. K.; Gorin, F. A.; Cala, P. M. (2000) Malignant Gliomas Display Altered pH Regulation by NHE1 Compared with Nontransformed Astrocytes. Am. J. Physiol. Cell Physiol. 278, C676-88.

(16) Lowe, P. R.; Sansom, C. E.; Schwalbe, C. H.; Stevens, M. F. G.; Clark, A. S. (1992) Antitumor Imidazotetrazines. 25. Crystal Structure of 8-Carbamoyl-3-Methylimidazo[5,1-d]-1,2,3,5-Tetrazin-4(3H)-One (Temozolomide) and Structural Comparisons with the Related Drugs Mitozolomide and DTIC. J. Med. Chem. 35, 3377-3382.

(17) Suppasansatorn, P.; Wang, G.; Conway, B. R.; Wang, W.; Wang, Y. (2006) Skin Delivery Potency and Antitumor Activities of Temozolomide Ester Prodrugs. Cancer Lett. 244, 42-52.

(18) Liu, D.; Yang, J. G.; Cheng, J.; Zhao, L. X. (2010) Synthesis and Antitumor Activity of 3-Methyl-4-Oxo-3,4-Dihydroimidazo [5,1-d][1,2,3,5]Tetrazine-8-Carboxylates and -Carboxamides. Molecules 15, 9427-9436.

(19) Hummersone, M. G.; Stevens, M. F. G.; Cousin, D. Preparation of 3-Substituted-3H-Imidazo[5,1-d][1,2,3,5]Tetrazin-4-One Compounds for Treating Proliferative Disorders. WO 2010149968, 2010.

(20) O'Reilly, S. M.; Newlands, E. S.; Brampton, M.; Glaser, M. G.; Rice-Edwards, J. M.; Illingworth, R. D.; Richards, P. G.; Kennard, C.; Colquhoun, I. R.; Lewis, P.; Stevens, M. F. G. (1993) Temozolomide: A New Oral Cytotoxic Chemotherapeutic Agent with Promising Activity against Primary Brain Tumours. Eur. J. Cancer 29, 940-942.

(21) Bleehen, N. M.; Newlands, E. S.; Lee, S. M.; Thatcher, N.; Selby, P.; Calvert, A. H.; Rustin, G. J. S.; Brampton, M.; Stevens, M. F. G. (1995) Cancer Research Campaign Phase II Trial of Temozolomide in Metastatic Melanoma. J. Clin. Oncol. 13, 910-913.

(22) Shealy, Y. F.; Struck, R. F.; Holum, L. B.; Montgomery, J. A. (1961) Synthesis of Potential Anticancer Agents. XXIX. 5-Diazoimidazole-4-Carboxamide and 5-Diazo-v-Triazole-4-Carboxamide. J. Org. Chem. 26, 2396-2401.

(23) Shechter, H.; Magee, W. L.; Rao, C. B.; Glinka, J.; Hui, H.; Amick, T. J.; Fiscus, D.; Kakodkar, S.; Nair, M. (1987) Dipolar Cycloaddition Reactions of Diazoazoles with Electron-Rich and with Strained Unsaturated Compounds. J. Org. Chem. 52, 5538-5548.

(24) Fulmer Shealy, Y.; Krauth, C. A.; Montgomery, J. A. (1962) Imidazoles. I. Coupling Reactions of 5-Diazoimidazole-4-Carboxamide. J. Org. Chem. 27, 2150-2154.

(25) Stevens, M. F.; Hickman, J. A.; Stone, R.; Gibson, N. W.; Baig, G. U.; Lunt, E.; Newton, C. G. (1984) Antitumor Imidazotetrazines. 1. Synthesis and Chemistry of 8-Carbamoyl-3-(2-Chloroethyl)Imidazo[5,1-d]-1,2,3,5-Tetrazin-4(3H)-One, a Novel Broad-Spectrum Antitumor Agent. J. Med. Chem. 27, 196-201.

(26) Lunt, E.; Newton, C. G.; Smith, C.; Stevens, G. P.; Stevens, M. F. G.; Straw, C. G.; Walsh, R. J. A.; Warren, P. J.; Fizames, C.; Lavelle, F.; Langdon, S. P.; Vickers, L. M. (1987) Antitumor Imidazotetrazines. 14. Synthesis and Antitumor Activity of 6- and 8-Substituted Imidazo[5,1-d]-1,2,3,5-Tetrazinones and 8-Substituted Pyrazolo[5,1-d]-1,2,3,5-Tetrazinones. J. Med. Chem. 30, 357-366.

(27) Moseley, C. K.; Carlin, S. M.; Neelamegam, R.; Hooker, J. M. (2012) An Efficient and Practical Radiosynthesis of [11C]Temozolomide. Org. Lett. 14, 5872-5875.

(28) Horspool, K. R.; Stevens, M. F. G.; Baig, G. U.; Newton, C. G.; Lunt, E.; Walsh, R. J. A.; Pedgrift, B. L.; Lavelle, F.; Fizames, C. (1990) Antitumor Imidazotetrazines. 20. Preparation of the 8-Acid Derivative of Mitozolomide and Its Utility in the Preparation of Active Antitumor Agents. J. Med. Chem. 33, 1393-1399.

(29) Langnel, D. A. F.; Arrowsmith, J.; Stevens, M. F. G. (2000) Antitumor Imidazotetrazines. 38. New 8-Substituted Derivatives of the Imidazo[5,1-d]-1,2,3,5-Tetrazines Temozolomide and Mitozolomide. ARKIVOC No. iii, 421-437.

(30) Stevens, M. A.; Giner-Sorolla, A.; Smith, H. W.; Bosworth Brown, G. (1962) Purine N-Oxides. X. The Effect of Some Substituents on Stability and Reactivity. J. Org. Chem. 27, 567-572.

(31) Xie, Y.; Bergstrom, T.; Jiang, Y.; Johansson, P.; Marinescu, V. D.; Lindberg, N.; Segerman, A.; Wicher, G.; Niklasson, M.; Baskaran, S.; Sreedharan, S.; Everlien, I.; Kastemar, M.; Hermansson, A.; Elfineh, L.; Libard, S.; Holland, E. C.; Hesselager, G.; Alafuzoff, I.; Westermark, B.; Nelander, S.; Forsberg-Nilsson, K.; Uhrbom, L. (2015) The Human Glioblastoma Cell Culture Resource: Validated Cell Models Representing All Molecular Subtypes. EBioMedicine 2, 1351-1363.

(32) Pardridge, W. M. (2005) The Blood-Brain Barrier: Bottleneck in Brain Drug Development. NeuroRX 2, 3-14.

(33) Norinder, U.; Haeberlein, M. (2002) Computational Approaches to the Prediction of the Blood-Brain Distribution. Adv. Drug Deliv. Rev. 54, 291-313.

(34) West, D. C.; Qin, Y.; Peterson, Q. P.; Thomas, D. L.; Palchaudhuri, R.; Morrison, K. C.; Lucas, P. W.; Palmer, A. E.; Fan, T. M.; Hergenrother, P. J. (2012) Differential Effects of Procaspase-3 Activating Compounds in the Induction of Cancer Cell Death. Mol. Pharm. 9, 1425-1434.

(35) Egan, W. J.; Merz, K. M.; Baldwin, J. J. (2000) Prediction of Drug Absorption Using Multivariate Statistics. J. Med. Chem. 43, 3867-3877.

(36) Tian, S.; Wang, J.; Li, Y.; Li, D.; Xu, L.; Hou, T. (2015) The Application of in Silico Drug-Likeness Predictions in Pharmaceutical Research. Adv. Drug Deliv. Rev. 86, 2-10.

(37) Daina, A.; Zoete, V. (2016) A BOILED-Egg To Predict Gastrointestinal Absorption and Brain Penetration of Small Molecules. ChemMedChem 11, 1117-1121.

(38) Alifrangis, L. H.; Christensen, I. T.; Berglund, A.; Sandberg, M.; Hovgaard, L.; Frokjaer, S. (2000) Structure—Property Model—for Membrane Partitioning of Oligopeptides. J. Med. Chem. 43, 103-113.

(39) Wager, T. T.; Hou, X.; Verhoest, P. R.; Villalobos, A. (2010) Moving beyond Rules: The Development of a Central Nervous System Multiparameter Optimization (CNS MPO) Approach to Enable Alignment of Druglike Properties. ACS Chem. Neurosci. 1, 435-449.

(40) Wager, T. T.; Hou, X.; Verhoest, P. R.; Villalobos, A. (2016) Central Nervous System Multiparameter Optimization Desirability: Application in Drug Discovery. ACS Chem. Neurosci. 7, 767-775.

(41) Reyderman, L.; Statkevich, P.; Thonoor, C. M.; Patrick, J.; Batra, V. K.; Wirth, M. (2004) Disposition and Pharmacokinetics of Temozolomide in Rat. Xenobiotica 34, 487-500.

(42) Rai, R.; Banerjee, M.; Wong, D. H.; McCullagh, E.; Gupta, A.; Tripathi, S.; Riquelme, E.; Jangir, R.; Yadav, S.; Raja, M.; Melkani, P.; Dixit, V.; Patil, U.; Shrivastava, R.; Middya, S.; Olivares, F.; Guerrero, J.; Surya, A.; Pham, S. M.; Bernales, S.; Protter, A. A.; Hung, D. T.; Chakravarty, S. (2016) Temozolomide Analogs with Improved Brain/Plasma Ratios—Exploring the Possibility of Enhancing the Therapeutic Index of Temozolomide. Bioorganic Med. Chem. Lett. 26, 5103-5109.

(43) Kim, S. S.; Rait, A.; Kim, E.; DeMarco, J.; Pirollo, K. F.; Chang, E. H. (2015) Encapsulation of Temozolomide in a Tumor-Targeting Nanocomplex Enhances Anti-Cancer Efficacy and Reduces Toxicity in a Mouse Model of Glioblastoma. Cancer Lett. 369, 250-258.

(44) Stevens, M. F.; Hickman, J. A.; Langdon, S. P.; Chubb, D.; Vickers, L.; Stone, R.; Baig, G.; Goddard, C.; Gibson, N. W.; Slack, J. A. (1987) Antitumor Activity and Pharmacokinetics in Mice of 8-Carbamoyl-3-Methyl-Imidazo [5,1-d]-1,2,3,5-Tetrazin-4(3H)-One (CCRG 81045; M & B 39831), a Novel Drug with Potential as an Alternative to Dacarbazine. Cancer Res. 47, 5846-5852.

(45) Bobola, M. S.; Tseng, S. H.; Blank, a; Berger, M. S.; Silber, J. R. (1996) Role of 06-Methylguanine-DNA Methyltransferase in Resistance of Human Brain Tumor Cell Lines to the Clinically Relevant Methylating Agents Temozolomide and Streptozotocin. Clin. Cancer Res. 2, 735-741.

(46) Kanzawa, T.; Bedwell, J.; Kondo, Y.; Kondo, S.; Germano, I. M. (2003) Inhibition of DNA Repair for Sensitizing Resistant Glioma Cells to Temozolomide. J. Neurosurg. 99, 1047-1052.

(47) Binder, Z. A.; Wilson, K. M.; Salmasi, V.; Orr, B. A.; Eberhart, C. G.; Siu, I. M.; Lim, M.; Weingart, J. D.; Quinones-Hinojosa, A.; Bettegowda, C.; Kassam, A. B.; Olivi, A.; Brem, H.; Riggins, G. J.; Gallia, G. L. (2016) Establishment and Biological Characterization of a Panel of Glioblastoma Multiforme (GBM) and GBM Variant Oncosphere Cell Lines. PLoS One 11, e0150271.

(48) Scaringi, C.; De Sanctis, V.; Minniti, G.; Enrici, R. M. (2013) Temozolomide-Related Hematologic Toxicity. Onkologie 36, 444-449.

(49) Thomas, R. P.; Recht, L.; Nagpal, S. (2013) Advances in the Management of Glioblastoma: The Role of Temozolomide and MGMT Testing. Clin. Pharmacol., 5, 1-9.

(50) Chamberlain, M. C. (2010) Temozolomide: Therapeutic Limitations in the Treatment of Adult High-Grade Gliomas. Expert Rev. Neurother. 10, 1537-1544.

(51) Li, R.; Tang, D.; Zhang, J.; Wu, J.; Wang, L.; Dong, J. (2014) The Temozolomide Derivative 2T-P400 Inhibits Glioma Growth via Administration Route of Intravenous Injection. J. Neurooncol. 116, 25-30.

(52) Cheng, Y.; Sk, U. H.; Zhang, Y.; Ren, X.; Zhang, L.; Huber-Keener, K. J.; Sun, Y. W.; Liao, J.; Amin, S.; Sharma, A. K.; Yang, J. M. (2012) Rational Incorporation of Selenium into Temozolomide Elicits Superior Antitumor Activity Associated with Both Apoptotic and Autophagic Cell Death. PLoS One 7, e35104.

(53) Cho, H.-Y.; Wang, W.; Jhaveri, N.; Lee, D. J.; Sharma, N.; Dubeau, L.; Schonthal, A. H.; Hofman, F. M.; Chen, T. C. (2014) NEO212, Temozolomide Conjugated to Perillyl Alcohol, Is a Novel Drug for Effective Treatment of a Broad Range of Temozolomide-Resistant Gliomas. Mol. Cancer Ther. 13, 2004-2017.

(54) Owonikoko, T. K.; Arbiser, J.; Zelnak, A.; Shu, H.-K. G.; Shim, H.; Robin, A. M.; Kalkanis, S. N.; Whitsett, T. G.; Salhia, B.; Tran, N. L.; Ryken, T.; Moore, M. K.; Egan, K. M.; Olson, J. J. (2014) Current Approaches to the Treatment of Metastatic Brain Tumours. Nat. Rev. Clin. Oncol. 11, 203-222.

(55) Thomas, A.; Tanaka, M.; Trepel, J.; Reinhold, W. C.; Rajapakse, V. N.; Pommier, Y. (2017) Temozolomide in the Era of Precision Medicine. Cancer Res., 77, 823-826.

REFERENCES TO EXAMPLES (1) Xie, Y.; Bergstrom, T.; Jiang, Y.; Johansson, P.; Marinescu, V. D.; Lindberg, N.; Segerman, A.; Wicher, G.; Niklasson, M.; Baskaran, S.; et al. (2015) The Human Glioblastoma Cell Culture Resource: Validated Cell Models Representing All Molecular Subtypes. EBioMedicine 2, 1351-1363.

(2) Binder, Z. A.; Wilson, K. M.; Salmasi, V.; Orr, B. A.; Eberhart, C. G.; Siu, I. M.; Lim, M.; Weingart, J. D.; Quinones-Hinojosa, A.; Bettegowda, C.; et al. (2016) Establishment and Biological Characterization of a Panel of Glioblastoma Multiforme (GBM) and GBM Variant Oncosphere Cell Lines. PLoS One 11, e0150271.

(3) Quinlivan, E. P.; Gregory, J. F. (2008) DNA Digestion to Deoxyribonucleoside: A Simplified One-Step Procedure. Anal. Biochem. 373, 383-385.

(4) Arrowsmith, J.; Jennings, S. A.; Clark, A. S.; Stevens, M. F. G. (2002) Antitumor Imidazotetrazines. 41.1 Conjugation of the Antitumor Agents Mitozolomide and Temozolomide to Peptides and Lexitropsins Bearing DNA Major and Minor Groove-Binding Structural Motifs. J. Med. Chem. 45, 5458-5470.

(5) Wang, Y.; Conway, B.; Suppasansatorn, P. Synthesis of Temozolomide Esters as Potent Anticancer Pro-Drugs for Topical and Transdermal Applications in Treatments of Cancers. US 2006/0047117 A1, 2006.

(6) Langnel, D. A. F.; Arrowsmith, J.; Stevens, M. F. G. (2000) Antitumor Imidazotetrazines. 38. New 8-Substituted Derivatives of the Imidazo[5,1-d]-1,2,3,5-Tetrazines Temozolomide and Mitozolomide. ARKIVOC No. iii, 421-437.

(7) Jiao, Y. G.; Yu, H. T. (2001) Methyltrioxorhenium (MeReO3) Catalyzed Selective Oxidation of Purine and Related Compounds into Their N-Oxides. Synlett No. 1, 73-74.

(8) Stevens, M. A.; Giner-Sorolla, A.; Smith, H. W.; Bosworth Brown, G. (1962) Purine N-Oxides. X. The Effect of Some Substituents on Stability and Reactivity1. J. Org. Chem. 27, 567-572.

(9) Liu, D.; Yang, J. G.; Cheng, J.; Zhao, L. X. (2010) Synthesis and Antitumor Activity of 3-Methyl-4-Oxo-3, 4-Dihydroimidazo [5,1-d][1,2,3,5]Tetrazine-8-Carboxylates and -Carboxamides. Molecules 15, 9427-9436.

(10) Marasco, C. J.; Pera, P. J.; Spiess, A. J.; Bernacki, R.; Sufrin, J. R. (2005) Improved Synthesis of β-D-6-Methylpurine Riboside and Antitumor Effects of the β-D- and α-D-Anomers. Molecules 10, 1015-1020.

(11) Hummersone, Marc Geoffery; Stevens, Malcolm Francis Graham; Cousin, D. Preparation of 3-Substituted-3H-Imidazo[5,1-d][1,2,3,5]Tetrazin-4-One Compounds for Treating Proliferative Disorders. WO 2010/149968, 2010.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula (I):

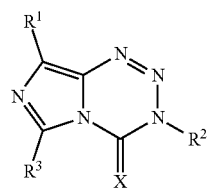

(I)

or a pharmaceutically acceptable salt thereof, wherein:
$R^1$ is 5- or 6-membered heterocycloalkyl, wherein the 5- or 6-membered heterocycloalkyl is optionally substituted with one or more substituents independently selected from the group consisting of F, Cl, Br, I, CN, $NO_2$, $C_1$-$C_6$ alkyl, $C_1$-$C_6$ haloalkyl, $C_2$-$C_6$ alkenyl, $C_2$-$C_6$ alkynyl, $(CH2)_{1-2}NHC(O)R'$, $C(NH)N(R')_2$, $C(NOR')R'$, $C(O)R'$, $C(O)CH_2C(O)R'$, $C(O)C(O)R'$, $C(O)N(R')_2$, $C(O)N(OR)R'$, $C(O)OR'$, $C(S)R'$, $C(S)N(R')_2$, $N(R')_2$, $NR'C(O)R'$, $NR'C(O)N(R')_2$, $NR'C(O)OR''$, $NR'C(S)R'$, $NR'C(S)(R')_2$, $NR'NR'C(O)R'$, $NR'NR'CON(R')_2$, $NR'NR'C(O)OR'$, $NR'S(O)_2R'$, $NR'S(O)_2N(R')_2$, $N[C(O)R']C(O)R'$, $N(OR')R'$, $OR'$, $OCF_3$, $—OCH_2O—$, $—OCH_2CH_2O—$, $OC(O)R'$, $OC(O)N(R')_2$, $=O$, $SR'$, $S(O)R'$, $S(O)_2R'$, $S(O)_2N(R')_2$, $S(O)_2OR'$, $=S$, and $C_3$-$C_6$ cycloalkyl;

$R^2$ is $C_1$-$C_6$ alkyl, $C_2$-$C_6$ alkenyl, $C_2$-$C_6$ alkynyl, or $C_3$-$C_6$ cycloalkyl;
wherein the $C_1$-$C_6$ alkyl, $C_2$-$C_6$ alkenyl, or $C_2$-$C_6$ alkynyl is optionally substituted with one or more substituents independently selected from the group consisting of F, Cl, Br, I, CN, $NO_2$, $(CH_2)_{1-2}NHC(O)R'$, $C(NH)N(R')_2$, $C(NOR')R'$, $C(O)R'$, $C(O)CH_2C(O)R'$, $C(O)C(O)R'$, $C(O)N(R')_2$, $C(O)N(OR)R'$, $C(O)OR'$, $C(S)R'$, $C(S)N(R')_2$, $N(R')_2$, $NR'C(O)R'$, $NR'C(O)N(R')_2$, $NR'C(O)OR'$, $NR'C(S)R'$, $NR'C(S)N(R')_2$, $NR'NR'C(O)R'$, $NR'NR'CON(R')_2$, $NR'NR'C(O)OR'$, $NR'S(O)_2R'$, $NR'S(O)_2N(R')_2$, $N[C(O)R']C(O)R'$, $N(OR')R'$, $OR'$, $OCF_3$, $—OCH_2O—$, $—OCH_2CH_2O—$, $OC(O)R'$, $OC(O)N(R')_2$, $SR'$, $S(O)R'$, $S(O)_2R'$, $S(O)_2N(R')_2$, $S(O)_2OR'$, and $C_3$-$C_6$ cycloalkyl; and
wherein the $C_3$-$C_6$ cycloalkyl is optionally substituted with one or more substituents independently selected from the group consisting of F, Cl, Br, I, CN, $NO_2$, $C_1$-$C_6$ alkyl, $C_1$-$C_6$ haloalkyl, $C_2$-$C_6$ alkenyl, $C_2$-$C_6$ alkynyl, $(CH_2)_{1-2}NHC(O)R'$, $C(NH)N(R')_2$, $C(NOR')R'$, $C(O)R'$, $C(O)CH_2C(O)R'$, $C(O)C(O)R'$, $C(O)N(R')_2$, $C(O)N(OR)R'$, $C(O)OR'$, $C(S)R'$, $C(S)N(R')_2$, $N(R')_2$, $NR'C(O)R'$, $NR'C(O)N(R')_2$, $NR'C(O)OR'$, $NR'C(S)R'$, $NR'C(S)N(R')_2$, $NR'NR'C(O)R'$, $NR'NR'CON(R')_2$, $NR'NR'C(O)OR'$, $NR'S(O)_2R'$, $NR'S(O)_2N(R')_2$, $N[C(O)R']C(O)R'$, $N(OR')R'$, $OR'$, $OCF_3$, $—OCH_2O—$, $—OCH_2CH_2O—$, $OC(O)R'$, $OC(O)N(R')_2$, $=O$, $O(phenyl)$, $SR'$, $S(O)R'$, $S(O)_2R'$, $S(O)_2N(R')_2$, $S(O)_2OR'$, $=S$, and $C_3$-$C_6$ cycloalkyl;

$R^3$ is H, $C_1$-$C_6$ alkyl, $C_2$-$C_6$ alkenyl, $C_2$-$C_6$ alkynyl, or $C_3$-$C_6$ cycloalkyl;
wherein the $C_1$-$C_6$ alkyl, $C_2$-$C_6$ alkenyl, or $C_2$-$C_6$ alkynyl is optionally substituted with one or more substituents independently selected from the group consisting of F, Cl, Br, I, CN, $NO_2$, $(CH_2)_{1-2}NHC(O)R'$, $C(NH)N(R')_2$, $C(NOR')R'$, $C(O)R'$, $C(O)CH_2C(O)R'$, $C(O)C(O)R'$, $C(O)N(R')_2$, $C(O)N(OR)R'$, $C(O)OR'$, $C(S)R'$, $C(S)N(R')_2$, $N(R')_2$, $NR'C(O)R'$, $NR'C(O)N(R')_2$, $NR'C(O)OR'$, $NR'C(S)R'$, $NR'C(S)N(R')_2$, $NR'NR'C(O)R'$, $NR'NR'CON(R')_2$, $NR'NR'C(O)OR'$, $NR'S(O)_2R'$, $NR'S(O)_2N(R')_2$, $N[C(O)R']C(O)R'$, $N(OR')R'$, $OR'$, $OCF_3$, $—OCH_2O—$, $—OCH_2CH_2O—$, $OC(O)R'$, $OC(O)N(R')_2$, $SR'$, $S(O)R'$, $S(O)_2R'$, $S(O)_2N(R')_2$, $S(O)_2OR'$, and $C_3$-$C_6$ cycloalkyl; and
wherein the $C_3$-$C_6$ cycloalkyl is optionally substituted with one or more substituents independently selected from the group consisting of F, Cl, Br, I, CN, $NO_2$, $C_1$-$C_6$ alkyl, $C_1$-$C_6$ haloalkyl, $C_2$-$C_6$ alkenyl, $C_2$-$C_6$ alkynyl, $(CH_2)_{1-2}NHC(O)R'$, $C(NH)N(R')_2$, $C(NOR')R'$, $C(O)R'$, $C(O)CH_2C(O)R'$, $C(O)C(O)R'$, $C(O)N(R')_2$, $C(O)N(OR)R'$, $C(O)OR'$, $C(S)R'$, $C(S)N(R')_2$, $N(R')_2$, $NR'C(O)R'$, $NR'C(O)N(R')_2$, $NR'C(O)OR'$, $NR'C(S)R'$, $NR'C(S)N(R')_2$, $NR'NR'C(O)R'$, $NR'NR'CON(R')_2$, $NR'NR'C(O)OR'$, $NR'S(O)R'$, $NR'S(O)_2N(R')_2$, $N[C(O)R']C(O)R'$, $N(OR')R'$, $OR'$, $OCF_3$, $—OCH_2O—$, $—OCH_2CH_2O—$, $OC(O)R'$, $OC(O)N(R')_2$, $=O, SR'$, $S(O)R'$, $S(O)_2R'$, $S(O)_2N(R')_2$, $S(O)_2OR'$, $=S$, and $C_3$-$C_6$ cycloalkyl;

each R' is independently H, C$_1$-C$_6$ alkyl, C$_2$-C$_6$ alkenyl, or C$_2$-C$_6$ alkynyl; and X is O or S.

2. The compound of claim 1, or a pharmaceutically acceptable salt thereof, wherein R$^2$ is C$_1$-C$_6$ alkyl.

3. The compound of claim 1, or a pharmaceutically acceptable salt thereof, wherein R$^2$ is unbranched C$_2$-C$_6$ alkyl, unbranched C$_2$-C$_6$ alkenyl, or unbranched C$_2$-C$_6$ alkynyl.

4. The compound of claim 1, or a pharmaceutically acceptable salt thereof, wherein R$^2$ is CH$_2$C≡CH, CH$_2$CH$_2$C≡2CH, or CH$_2$C≡2CCH$_3$.

5. A method for treating a cancer in a subject, wherein the method comprises administering to the subject in need thereof a therapeutically effective amount of a compound of claim 1, or a pharmaceutically acceptable salt thereof.

6. The method of claim 5, wherein the cancer is glioblastoma (GBM).

7. A compound of Formula (I):

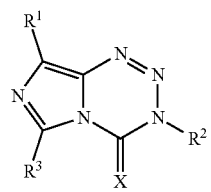

(I)

or a pharmaceutically acceptable salt thereof,
wherein:
R$^1$ is halo;
R$^2$ is C$_1$-C$_6$ alkyl, C$_2$-C$_6$ alkenyl, C$_2$-C$_6$ alkynyl, or C$_3$-C$_6$ cycloalkyl;
   wherein the C$_1$-C$_6$ alkyl, C$_2$-C$_6$ alkenyl, or C$_2$-C$_6$ alkynyl is optionally substituted with one or more substituents independently selected from the group consisting of F, Cl, Br, I, CN, NO$_2$, (CH$_2$)$_{1-2}$NHC(O) R', C(NH)N(R')$_2$, C(NOR')R', C(O)R', C(O)CH$_2$C(O) R', C(O)C(O)R', C(O)N(R')$_2$, C(O)N(OR)R', C(O) OR', C(S)R', C(S)N(R')$_2$, N(R')$_2$, NR'C(O)R', NR'C (O)N(R')$_2$, NR'C(O)OR', NR'C(S)R', NR'C(S) N(R')$_2$, NR'NR'C(O)R', NR'NR'CON(R')$_2$, NR'NR'C (O)OR', NR'S(O)$_2$R', NR'S(O)$_2$N(R')$_2$, N[C(O)R']C (O)R', N(OR')R', OR', OCF$_3$, —OCH$_2$O—, —OCH$_2$CH$_2$O—, OC(O)R', OC(O)N(R')$_2$, SR', S(O)R', S(O)$_2$R', S(O)$_2$N(R')$_2$, S(O)$_2$OR', and C$_3$-C$_6$ cycloalkyl; and
   wherein the C$_3$-C$_6$ cycloalkyl is optionally substituted with one or more substituents independently selected from the group consisting of F, Cl, Br, I, CN, NO2, C$_1$-C$_6$ alkyl, C$_1$-C$_6$ haloalkyl, C$_2$-C$_6$ alkenyl, C$_2$-C$_6$ alkynyl, (CH$_2$)$_{1-2}$NHC(O)R', C(NH)N(R')$_2$, C(NOR')R', C(O)R', C(O)CH$_2$C(O)R', C(O)C(O)R', C(O)N(R')$_2$, C(O)N(OR)R', C(O)OR', C(S)R', C(S) N(R')$_2$, N(R')$_2$, NR'C(O)R', NR'C(O)N(R')$_2$, NR'C (O)OR', NR'C(S)R', NR'C(S)N(R')$_2$, NR'NR'C(O)R', NR'NR'CON(R')$_2$, NR'NR'C(O)OR', NR'S(O)$_2$R', NR'S(O)$_2$N(R')$_2$, N[C(O)R']C(O)R', N(OR') R', OR', OCF$_3$, —OCH$_2$O—, —OCH$_2$CH$_2$O—, OC(O)R', OC(O)N(R')$_2$, =O, O(phenyl), SR', S(O)R', S(O)$_2$R', S(O)$_2$N(R')$_2$, S(O)$_2$OR', =2S, and C$_3$-C$_6$cycloalkyl;

R$^3$ is H, C$_1$-C$_6$ alkyl, C$_2$-C$_6$ alkenyl, C$_2$-C$_6$ alkynyl, or C$_3$-C$_6$ cycloalkyl;
   wherein the C$_1$-C$_6$ alkyl, C$_2$-C$_6$ alkenyl, or C$_2$-C$_6$ alkynyl is optionally substituted with one or more substituents independently selected from the group consisting of F, Cl, Br, I, CN, NO$_2$, (CH$_2$)$_{1-2}$NHC(O)R', C(NH)N(R')$_2$, C(NOR')R', C(O)R', C(O)CH$_2$C(O) R', C(O)C(O)R', C(O)N(R')$_2$, C(O)N(OR)R', C(O) OR', C(S)R', C(S)N(R')$_2$, N(R')$_2$, NR'C(O)R', NR'C (O)N(R')$_2$, NR'C(O)OR', NR'C(S)R', NR'C(S) N(R')$_2$, NR'NR'C(O)R', NR'NR'CON(R')$_2$, NR'NR'C (O)OR', NR'S(O)$_2$R', NR'S(O)$_2$N(R')$_2$, N[C(O)R']C (O)R', N(OR')R', OR', OCF$_3$, —OCH$_2$O—, —OCH$_2$CH$_2$O—, OC(O)R', OC(O)N(R')$_2$, SR', S(O)R', S(O)$_2$R', S(O)$_2$N(R')$_2$, S(O)$_2$OR', and C$_3$-C$_6$ cycloalkyl; and
   the C$_3$-C$_6$ cycloalkyl is optionally substituted with one or more substituents independently selected from the group consisting of F, Cl, Br, I, CN, NO$_2$, C$_1$-C$_6$ alkyl, C$_1$-C$_6$ haloalkyl, C$_2$-C$_6$ alkenyl, C$_2$-C$_6$ alkynyl, (CH$_2$)$_{1-2}$NHC(O)R', C(NH)N(R')$_2$, C(NOR')R', C(O)R', C(O)CH$_2$C(O)R', C(O)C(O)R' C(O)N(R')$_2$, C(O)N(OR)R', C(O)OR', C(S)R', C(S)N(R')$_2$, N(R')$_2$, NR'C(O)R', NR'C(O)N(R')$_2$, NR'C(O)OR', NR'C(S)R', NR'C(S)N(R')$_2$, NR'NR'C(O)R', NR'NR'CON(R')$_2$, NR'NR'C(O)OR', NR'S(O)$_2$R', NR'S(O)$_2$N(R')$_2$, N[C(O)R']C(O)R', N(OR')R', OR', OCF$_3$, —OCH$_2$O—, —OCH$_2$CH$_2$O—, OC(O)R', OC(O)N(R')$_2$, =O, SR', S(O)R', S(O)$_2$R', S(O)$_2$N (R')$_2$, S(O)$_2$OR', '2 S, and C$_3$-C$_6$ cycloalkyl;

each R' is independently H, C$_1$-C$_6$ alkyl, C$_2$-C$_6$ alkenyl, or C$_2$-C$_6$ alkynyl; and X is O or S.

8. The compound of claim 7, or a pharmaceutically acceptable salt thereof, wherein R$^2$ is unbranched C$_2$-C$_6$ alkyl, unbranched C$_2$-C$_6$ alkenyl, or unbranched C$_2$-C$_6$ alkynyl.

9. The compound of claim 7, or a pharmaceutically acceptable salt thereof, wherein R$^2$ is CH$_2$C≡CH, CH$_2$CH$_2$C≡CH, or CH$_2$C≡CCH$_3$.

10. The compound of claim 7, wherein the compound is:

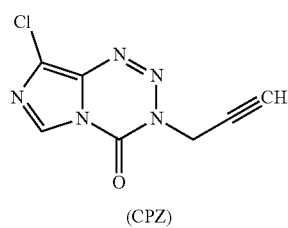

(CPZ)

or a pharmaceutically acceptable salt thereof.

11. A method for treating glioblastoma (GBM) in a subject, wherein the method comprises administering to the subject in need thereof a therapeutically effective amount of a compound of claim 7, or a pharmaceutically acceptable salt thereof.

12. A compound:
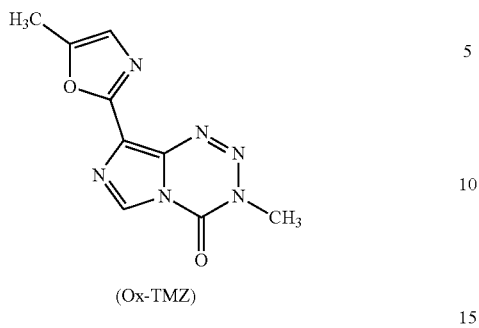
(Ox-TMZ)
or a pharmaceutically acceptable salt thereof.
13. A method for treating glioblastoma (GBM) in a subject, wherein the method comprises administering to the subject in need thereof a therapeutically effective amount of the compound of claim 12, or a pharmaceutically acceptable salt thereof.
\* \* \* \* \*

UNITED STATES PATENT AND TRADEMARK OFFICE
CERTIFICATE OF CORRECTION

Page 1 of 1

PATENT NO. : 12,234,240 B2
APPLICATION NO. : 18/067531
DATED : February 25, 2025
INVENTOR(S) : Paul J. Hergenrother, Timothy M. Fan and Riley L. Svec It is certified that error appears in the above-identified patent and that said Letters Patent is hereby corrected as shown below:

In the Claims

In Claim 4, at Column 57, Line 12, "$CH_2CH_2C\equiv2CH$, or $CH_2C\equiv2CCH_3$." should be -- $CH_2CH_2C=CH$, or $CH_2C\equiv CCH_3$. -- therefor.

In Claim 7, at Column 58, Line 2, "=2S," should be -- =S, -- therefor.

In Claim 7, at Column 58, Line 36, "'2 S," should be -- =S, -- therefor.

Signed and Sealed this
Fifteenth Day of April, 2025

Coke Morgan Stewart
*Acting Director of the United States Patent and Trademark Office*